(12) United States Patent
Sallee et al.

(10) Patent No.: US 6,353,000 B1
(45) Date of Patent: Mar. 5, 2002

(54) 11-HALO PROSTAGLANDINS FOR THE TREATMENT OF GLAUCOMA OR OCULAR HYPERTENSION

(75) Inventors: Verney L. Sallee, Burleson; Mark R. Hellberg, Arlington; Peter G. Klimko; Paul W. Zinke, both of Fort Worth, all of TX (US)

(73) Assignee: Alcon Laboratories, Inc., Fort Worth, TX (US)

( * ) Notice: Subject to any disclaimer, the term of this patent is extended or adjusted under 35 U.S.C. 154(b) by 0 days.

(21) Appl. No.: 09/284,533

(22) PCT Filed: Nov. 7, 1997

(86) PCT No.: PCT/US97/20672

§ 371 Date: Jun. 2, 1999

§ 102(e) Date: Jun. 2, 1999

(87) PCT Pub. No.: WO98/20880

PCT Pub. Date: May 22, 1998

Related U.S. Application Data

(60) Provisional application No. 60/030,505, filed on Nov. 12, 1996.

(51) Int. Cl.[7] .......................... A01N 43/16; A01N 43/08; A01N 43/30; A01N 43/26; C07D 453/02; C07D 209/02; C07D 209/04; C07D 209/44; C07D 333/52; C07D 333/56; C07D 333/16; C07D 311/04; C07D 307/00; C07D 69/00; C07D 61/06

(52) U.S. Cl. ................. 514/310; 549/399; 549/401; 549/429; 560/129; 562/503

(58) Field of Search .................. 514/305–310, 514/412, 416, 432, 443, 456, 461, 464, 465; 546/429, 134; 548/452, 469, 470, 482; 560/129; 562/503; 549/49, 51, 57, 78, 398, 399, 401

(56) References Cited

PUBLICATIONS

Thierauch et al, Prostaglandins, 35(6), 855–68, 1988.*

* cited by examiner

*Primary Examiner*—Alton Pryor
(74) *Attorney, Agent, or Firm*—Barry L. Copeland

(57) ABSTRACT

A method of treating glaucoma or ocular hypertension in a patient, which comprises administering to the patient a pharmaceutically effective amount of a compound of formula I:

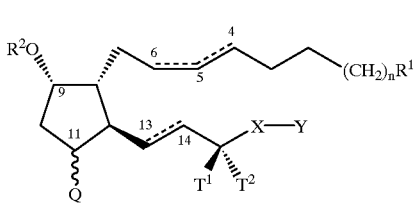

25 Claims, No Drawings

11-HALO PROSTAGLANDINS FOR THE TREATMENT OF GLAUCOMA OR OCULAR HYPERTENSION

This claims the benefit of Provisional application No. 60/030,505 filed Nov. 12, 1996. This appln is a 371 of PCT/US97/20672 filed Nov. 7, 1997.

BACKGROUND OF THE INVENTION

The present invention relates to novel compounds and methods for the treatment of glaucoma and ocular hypertension. In particular, the present invention relates to the use of certain 11-halo analogs of F series prostaglandins to treat glaucoma and ocular hypertension.

Glaucoma is a progressive disease which leads to optic nerve damage and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The causes of aqueous humor accumulation in the anterior chamber are not fully understood. It is known that elevated intraocular pressure ("IOP") can be at least partially controlled by administering drugs which either reduce the production of aqueous humor within the eye, such as beta-blockers and carbonic anhydrase inhibitors, or increase the outflow of aqueous humor from the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects such as nausea, dyspepsia, fatigue, and metabolic acidosis, which side effects can affect patient compliance and/or necessitate the termination of treatment. Another type of drug, beta-blockers, have increasingly become associated with serious pulmonary side effects attributable to their effects on beta-2 receptors in pulmonary tissue. Sympathomimetics, on the other hand, may cause tachycardia, arrhythmia and hypertension. Recently, certain prostaglandins and prostaglandin derivatives have been described in the art as being useful in reducing intraocular pressure. Typically, however, prostaglandin therapy for the treatment of elevated intraocular pressure is attended by undesirable side-effects, such as irritation and hyperemia of varying severity and duration. There is therefore a continuing need for therapies which control elevated intraocular pressure associated with glaucoma without the degree of undesirable side-effects attendant to most conventional therapies.

Prostaglandins are metabolite derivatives of arachidonic acid. Arachidonic acid in the body is converted to prostaglandin $G_2$, which is subsequently converted to prostaglandin $H_2$. Other naturally occurring prostaglandins are derivatives of .prostaglandin $H_2$. A number of different types of prostaglandins are known in the art including A, B, C, D, E, F, G, I and J-Series prostaglandins (EP 0 561 073 A1). Of interest in the present invention are compounds which are believed to exhibit IOP lowering mechanisms similar to those exhibited by $PGF_{2\alpha}$, an F-series prostaglandin of the following formula:

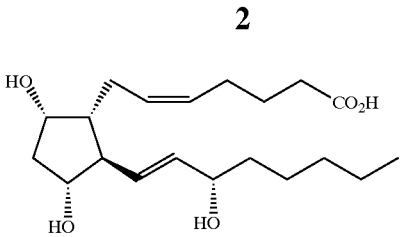

The relationship of $PGF_{2\alpha}$ receptor activation and IOP lowering effects is not well understood. It is believed by some that $PGF_{2\alpha}$ receptor activation leads to increased outflow of aqueous humor. Regardless of mechanism, $PGF_{2\alpha}$ and certain of its analogs have been shown to lower IOP (Giuffre, The Effects of Prostaglandin $F_{2\alpha}$ the Human Eye, *Graefe's Archive Ophthalmology*, volume 222, pages 139–141 (1985); and Kerstetter et al., Prostaglandin $F_{2\alpha}$-1-Isopropylester Lowers Intraocular Pressure Without Decreasing Aqueous Humor Flow, *American Journal of Ophthalmology*, volume 105, pages 30–34 (1988)). Thus, it has been of interest in the ophthalmic field to develop synthetic $PGF_{2\alpha}$ analogs with IOP lowering efficacy.

Synthetic $PGF_{2\alpha}$-type analogs have been pursued in the art (*Graefe's Archive Ophthalmology*, volume 229, pages 411–413 (1991)). Though $PGF_{2\alpha}$-type molecules lower IOP, these types of molecules have also been associated with undesirable side effects resulting from topical ophthalmic dosing. Such effects include an initial increase in IOP, breakdown of the blood aqueous barrier and conjunctival hyperemia (Alm, The Potential of Prostaglandin Derivatives in Glaucoma Therapy, *Current Opinion in Ophthalmology*, volume 4, No. 11, pages 44–50 (1993)). The binding of other types of molecules with the $PGF_{2\alpha}$ receptor may lead to IOP lowering effects, but with reduced or fewer side effects than those elicited by the above mentioned $PGF_{2\alpha}$-type analogs.

An agent which exhibits comparable or improved efficacy, but with reduced side effects when compared to other agents, is said to have an improved therapeutic profile. It is an object of this invention to provide a class of IOP lowering agents with an improved therapeutic profile over $PGF_{2\alpha}$ and methods of their use. It has now unexpectedly been discovered that the presently claimed 11-halo analogs of $PGF_{2\alpha}$ meet this objective. Although certain 11-halo prostaglandins are known in the art (Thierauch, et al., "Stable 9β- or 11α-Halogen-15-cyclohexyl-Prostaglandins with High Affinity to the $PGD_2$-Receptor," *Prostaglandins*, 35:6, 855 (June 1988); U.S. Pat. Nos. 4,870,104 and 4,983, 629; and EPO 561 073 A1), the surprisingly enhanced therapeutic profiles of such compounds and the novel compounds of the present invention in the treatment of glaucoma is neither disclosed nor suggested in that art.

SUMMARY OF THE INVENTION

The present invention is directed to compositions, including certain novel compounds, and methods of their use in treating glaucoma and ocular hypertension. In particular, the present invention provides certain classes of 11-halo prostaglandins having functional $PGF_{2\alpha}$ receptor agonist activity, and methods of their use in treating glaucoma and ocular hypertension.

DETAILED DESCRIPTION OF THE INVENTION

It has unexpectedly been found that 11-halo substituted $PGF_{2\alpha}$ analogs of the present invention exhibit an improved therapeutic profile in the treatment of glaucoma and ocular hypertension when compared to natural prostaglandins and many of their known analogs. The substituted PGF$_{2\alpha}$ analogs of the present invention have the following formula I:

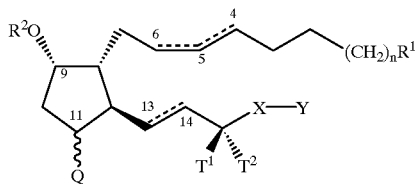

I wherein:
  n=0 or 2;
  R$^1$=CO$_2$R, CONR$^4$R$^5$, CH$_2$OR$^6$, or CH$_2$NR$^7$R$^8$; where:
    R=H or cationic salt moiety, or CO$_2$R forms an ophthalmically acceptable ester moiety;
    R$^4$, R$^5$=same or different=H or alkyl; R$^6$=H, acyl, or alkyl;
    R$^7$, R$^8$=same or different=H, acyl, or alkyl; with the proviso that if one of R$^7$, R$^8$=acyl, then the other=H or alkyl;
  Q=halo;
  one of T$^1$, T$^2$=H, and the other=OR$^3$, wherein R$^3$ is as defined below; or T$^1$ and T$^2$ together=O (i.e., a carbonyl);
  R$^2$, R$^3$=same or different=H, alkyl, or acyl;
  - - - =single or non-cumulated double bond, with the provisos that a double bond between carbons 4 and 5 may not be of the trans configuration; and that a double bond between carbons 13 and 14 may not be of the cis configuration;
  X=(CH$_2$)q or (CH$_2$)$_q$O, where q=1–6; and
  Y=a phenyl ring optionally substituted with alkyl, halo, trihalomethyl, alkoxy, acyl, acyloxy, amino, alkylamino, acylamino, or hydroxy; or
  X—Y=(CH$_2$)$_p$Y$^1$; where p=0–6; and

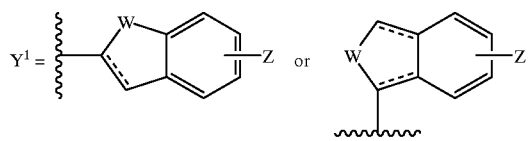

wherein:
  W=CH$_2$, O, S(O)$_m$, NR$^9$, CH$_2$CH$_2$, CH=CH, CH$_2$O, CH$_2$S(O)$_m$, CH=N, or CH$_2$NR$^9$; where m=0–2, and R$^9$=H, alkyl, or acyl;
  Z=H, alkyl, alkoxy, acyl, acyloxy, halo, trihalomethyl, amino, alkylamino, acylamino, or hydroxy; and
  - - - =single or double bond;

For purposes of the foregoing and following definitions, the term "pharmaceutically acceptable ester" means any ester that would, in appropriate doses, be suitable for therapeutic administration to a patient by conventional means without significant deleterious health consequences; and "ophthalmically acceptable ester" means any pharmaceutically acceptable ester that would be suitable for ophthalmic application, i.e. non-toxic and non-irritating. Preferred are alkyl esters. Most preferred are C$_2$–C$_4$ alkyl esters, and especially isopropyl esters. In addition, references to "carbons 4 and 5" and "carbons 13 and 14" shall mean the carbons so designated in the structural formulas even when n=2.

Preferred compounds for use in the methods and compositions of the present invention are those of formula II:

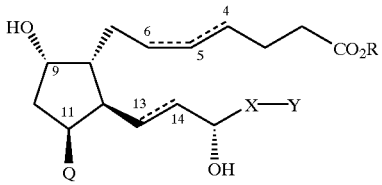

II wherein:

R=H; or CO$_2$R forms an ophthalmically acceptable ester moiety;
  - - - =single or non-cumulated double bond, with the provisos that a double bond between carbons 4 and 5 may not be of the trans configuration; and that a double bond between carbons 13 and 14 may not be of the cis configuration;
  Q=Cl or F;
  X=CH$_2$CH$_2$ or CH$_2$O; and
  Y=phenyl, optionally substituted with halo or trihalomethyl; or
  X—Y=(CH$_2$)$_p$Y$^1$; where p=0; and

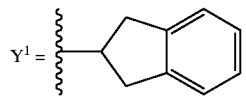

| Compound Number | Compound Name | Compound Structure |
|---|---|---|

-continued

| Compound Number | Compound Name | Compound Structure |
|---|---|---|
| III | (5Z, 13E)-(9S, 11S, 15R)-16-(3-Chlorophenoxy)-9,15-dihydroxy-11-fluoro-17,18,19,20-tetranor-5,13-prostadienoic acid isopropyl ester | 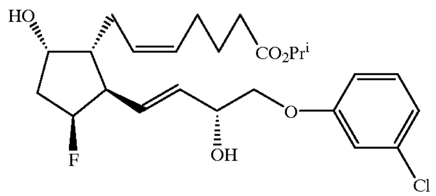 |
| IV | (5Z, 13E)-(9S, 11S, 15S)-9,15-Dihydroxy-11-fluoro-15-(2-indanyl)-16,17,18,19,20-pentanor-5,13-prostadienoic acid isopropyl ester | 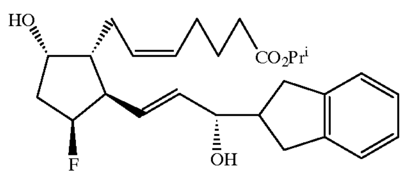 |
| V | (13E)-(9S, 11S, 15R)-16-(3-Chlorophenoxy)-9,15-dihydroxy-11-fluoro-17,18,19,20-tetranor-13-prostenoic acid isopropyl ester | 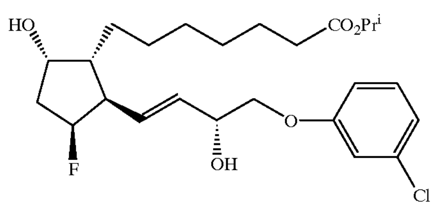 |
| VI | (5Z, 13E)-(9S, 11S, 15R)-9,15-Dihydroxy-11-fluoro-16-[(3-trifluoromethyl)phenoxy]-17,18,19,20-tetranor-5,13-prostadienoic acid methyl ester | 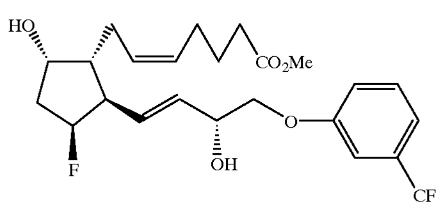 |
| VII | (4Z, 13E)-(9S, 11S, 5R)-9,15-Dihydroxy-11-fluoro-16-[(3-trifluoromethyl)phenoxy]-17,18,19,20-tetranor-4,13-prostadienoic acid isopropyl ester | 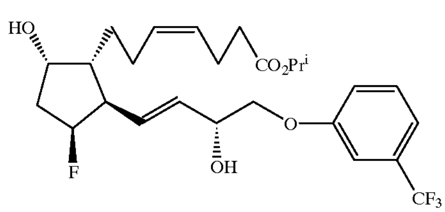 |
| VIII | (5Z, 13E)-(9S, 11S, 15R)-9,15-Dihydroxy-11-fluoro-16-[(3-trifluoromethyl)phenoxy]-17,18,19,20-tetranor-5,13-prostadienoic acid isopropyl ester | 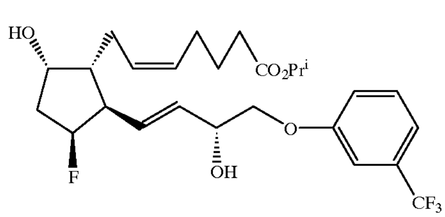 |
| IX | (5Z, 13E)-(9S, 11S, 15R)-11-Chloro-16-(3-chlorophenoxy)-9,15-dihydroxy-17,18,19,20-tetranor-5,13-prostadienoic acid isopropyl ester | 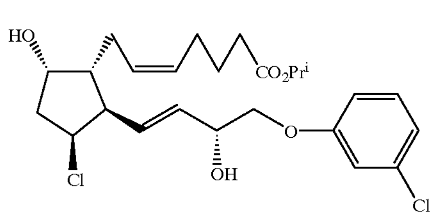 |

Included within the scope of the present invention are the individual enantiomers of the title compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis* by J. D. Morrison and J. W. Scott, Eds., Academic Press Publishers: New York, 1983–1985 (five volumes) and *Principles of Asymmetric Synthesis* by R. E. Gawley and J. Aube, Eds., Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC*, G. Subramanian, Ed., VCH Publishers: New York, 1994; *Chiral Separations by HPLC*, A. M. Krstulovic, Ed., Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution or even mixing samples having different enantiomeric ratios.

The compounds of the present invention believed to be novel are those possessing a cis double bond between carbons 4 and 5. Specifically, the compounds of formula I believed to be novel are those wherein:

n=0 or 2;

$R^1$=$CO_2R$, $CONR^4R^5$, $CH_2OR^6$, or $CH_2NR^7R^8$; where R=H or cationic salt moiety, or $CO_2R$ forms a pharmaceutically acceptable ester moiety; $R^4$, $R^5$=same or different=H or alkyl; $R^6$=H, acyl, or alkyl; $R^7$, $R^8$=same or different=H, acyl, or alkyl; with the proviso that if one of $R^7$, $R^8$=acyl, then the other=H or alkyl;

Q=halo;

one of $T^1$, $T^2$=H, and the other=$OR^3$, where $R^3$ is as defined below; or $T^1$ and $T^2$ together=O (i.e., a carbonyl);

$R^2$, $R^3$=same or different=H, alkyl, or acyl;

- - - =single or non-cumulated double bond, with the provisos that a double bond of the cis configuration is present between carbons 4 and 5; and that if a double bond is present between carbons 13 and 14, it is of the trans configuration;

X=$(CH_2)_q$ or $(CH_2)_qO$; where q=1–6; and

Y=a phenyl ring optionally substituted with alkyl, halo, trihalomethyl, alkoxy, acyl, acyloxy, amino, alkylamino, acylamino, or hydroxy; or X—Y=$(CH_2)_pY^1$; where p=0–6; and

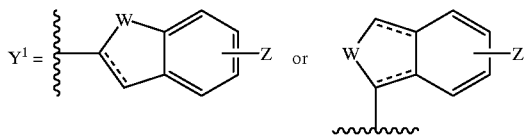

wherein:
W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;
Z=H, alkyl, alkoxy, acyl, acyloxy, halo, trihalomethyl, amino, alkylamino, acylamino, or hydroxy; and

- - - =single or double bond.

Similarly, novel compounds of the preferred class are those of formula II wherein:

R=H or alkyl;

- - - =single or non-cumulated double bond, with the provisos that a double bond of the cis configuration is present between carbons 4 and 5; and that if a double bond is present between carbons 13 and 14, it is of the trans configuration;

Q=Cl or F;

X=$CH_2CH_2$ or $CH_2O$; and

Y=phenyl, optionally substituted with halo or trihalomethyl; or

X—Y=$(CH_2)_pY^1$; where p=0; and

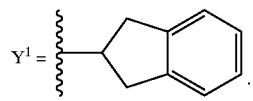

Other related PGFs within the scope of the present invention are known and their syntheses are either described in the literature or can be achieved by methods similar to those described in the literature or otherwise known to those of skill in the art. See, for example, U.S. Pat. Nos. 4,321,275; 4,870,104; and 4,983,629. The foregoing references are by this reference incorporated herein.

In the foregoing illustrations, as well as those provided hereinafter, wavy line attachments indicate that the configuration may be either alpha (α) or beta (β). The dashed lines on bonds between carbons 4 (C-4) and 5 (C-5), between carbons 5 (C-5) and 6 (C-6), and between carbons 13 (C-13) and 14 (C-14) indicate a single or double bond. Two solid lines present between carbons 5 (C-5) and 6 (C-6), between carbons 4 (C-4) and 5 (C-5), or between carbons 13 (C-13) and 14 (C-14) specify the configuration of the relevant double bond. Hatched lines, as used, eg., at carbon 9, indicate the α configuration. A solid triangular line, as used, eg., at carbon 12, indicates the β configuration.

In the following Examples 1–9, the following standard abbreviations are used: g=grams (mg=milligrams); mol=moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "MS" refers to mass spectrometry.

EXAMPLE 1

Synthesis of III

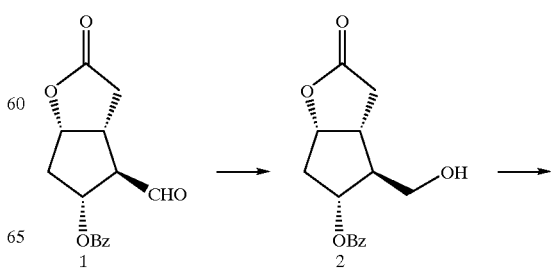

9
-continued

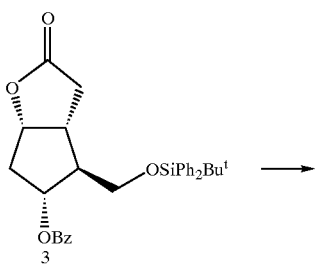
3

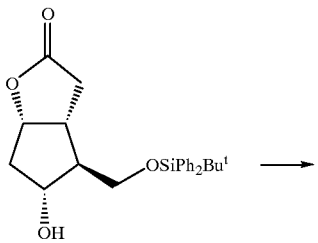
4

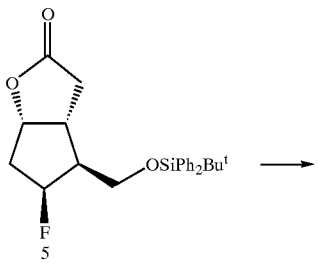
5

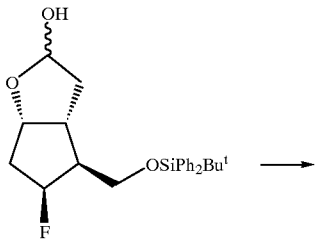
6

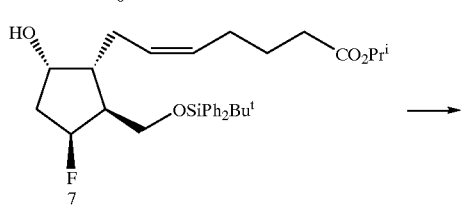
7

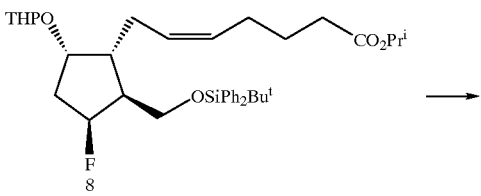
8

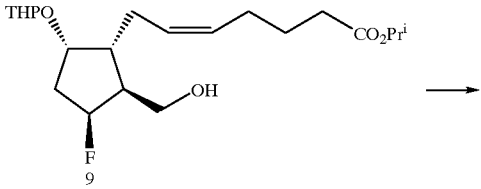
9

10
-continued

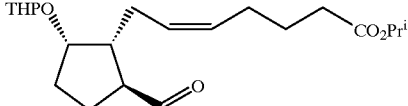
10

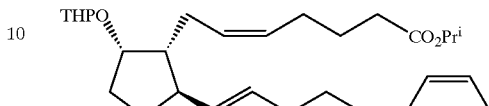
11

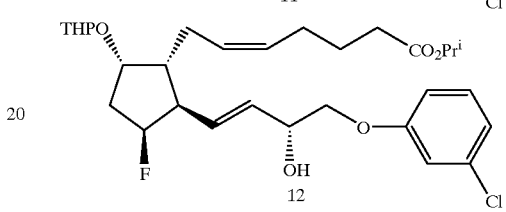
12

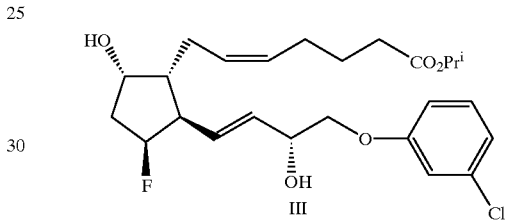
III

A. (3aR,4R,5R,6aS)-5-Benzoyloxy-4-(hydroxymethyl)hexahydro-2H-cycolopenta[b]furan-2-one (2)

To a suspension of sodium borohydride (650 mg, 17.1 mmol) in methanol (20 mL) at 0° C. (bath temperature) was added a solution of (3aR,4R,5R,6aS)-5-(benzoyloxy) hexahydro-2H-cyclopenta[b]furan-2-one-4-carboxaldehyde (1) (available from Cayman Chemical Company, Ann Arbor, Mich.) (3.5 g, 12.8 mmol) as a solution in 1:1 methanol:methylene chloride (40 mL). After 25 min, saturated citric acid was added cautiously (60 mL), the mixture was extracted with ethyl acetate (3×40 mL), the combined organic layers were washed with water (2×80 mL) and saturated brine (2×80 mL), dried (magnesium sulfate), filtered, and concentrated to afford 2 (2.43 g, 69%).

B. (3aR,4R,5R,6aS)-5-Benzoyloxy-4-[(t-butyldiphenylsiloxy)methyl]hexahydro-2H-cyclopenta[b]furan-2-one (3)

To a solution of 2 (2.40 g, 8.8 mmol), 4-(dimethylamino)pyridine (DMAP) (100 mg, 0.82 mmol), and imidazole (1.00 g, 14.7 mmol) in $CH_2Cl_2$ (35 mL) was added dropwise t-butyldiphenylchlorosilane (2.85 g, 10.4 mmol). After stirring overnight, the mixture was added to saturated ammonium chloride (40 mL), extracted with ethyl acetate (3×40 mL), dried (magnesium sulfate), filtered, concentrated, and chromatographed on a 14 cm tall×53 mm diameter silica gel eluting with 30% ethyl acetate in hexane to afford 3 (3.78 g, 83%).

C. (3aR,4R,5R,6aS)-4-[(t-Butyldiphenylsiloxy)methyl]-5-hydroxyhexahydro-2H-cyclopenta[b]furan-2-one (4)

To a solution of 3 (15.7 g, 30.0 mmol) in methanol (100 mL) was added potassium carbonate (4.14 g, 30.0 mmol).

After 1 h, saturated ammonium chloride (100 mL) and saturated brine (100 mL) were added, the mixture was extracted with methylene chloride (3×100 mL), dried (magnesium sulfate), filtered, concentrated, and chromatographed on a 15 cm tall×41 mm diameter silica gel column eluting with 40% ethyl acetate in hexane to afford 4 (9.93 g, 79%).

D. (3aR,4R,5S,6aS)-4-[(t-Butyldiphenylsiloxy)methyl]-5-fluorohexahydro-2H-cyclopenta[b]furan-2-one (5)

To a solution of (diethylamino)sulfur trifluoride (4.62 g, 28.6 mmol) in methylene chloride (27 mL) at −60° C. was added a solution of 4 (10.7 g, 26 mmol) dropwise as a solution in methylene chloride (27 mL). After 30 min, the reaction was warmed to room temperature and was stirred for an additional 18 h. To the solution was then cautiously added saturated sodium bicarbonate, the phases were separated, the aqueous layer was extracted with methylene chloride, the combined organic layers were dried (sodium sulfate), filtered, concentrated, and chromatographed on 300 g of silica gel eluting with 40% ethyl acetate in hexane to afford 5 contaminated with an olefinic by-product (total mass=6.5 g).

This sample of impure 5 was dissolved in a solution of acetone (59 mL) and water (7 mL). 4-Methylmorpholine N-oxide (3.81 g, 32 mmol) and osmium tetraoxide (4 mL of a 2.5 wt. % solution in t-butanol) were added, and the mixture was stirred for 19 h. Saturated sodium bisulfite (100 mL) and methylene chloride (200 mL) were added and a brown precipitate formed which was removed by filtration. The phases were separated, the aqueous was extracted with methylene chloride, the combined organic layers were dried (sodium sulfate), filtered, concentrated, and chromatographed on 300 g of silica gel eluting with 40% ethyl acetate in hexane to afford 5 (4.4 g, 41% yield from 4). $^{13}$C NMR (CDCl$_3$) δ176.44 (C), 135.53 (CH), 135.50 (CH), 133.16 (C), 133.03 (C), 129.93 (CH), 129.86 (CH), 127.83 (CH), 127.79 (CH), 95.63 (d,J=174 Hz, CH), 83.91 (CH), 61.56 (d, J=7 Hz, CH$_2$), 52.66 (d,J=19 Hz, CH), 40.25 (CH), 40.24 (d,J=22 Hz, CH$_2$), 34.25 (CH$_2$), 26.82 (CH$_3$), 19.15 (C).

E. (3 aR,4R,5S,6aS)-4-[(t-Butyldiphenylsiloxy)methyl]-5-fluoro-2-hydroxyhexahydro-2H-cyclopenta[b]furan (6)

To a solution of 5 (989 mg, 2.40 mmol) in toluene (15 mL) at −78° C. (bath temperature) was added dropwise a 1.5 M solution of diisobutylaluminum hydride (DIBAL) in toluene (2.4 mL, 3.6 mmol). After 1 h, methanol (2 mL) and ethyl acetate (2 mL) were added, the solution was warmed to room temperature, added to saturated sodium potassium tartarate (30 mL), and stirred for 30 min. The layers were separated, the aqueous phase was extracted with ethyl acetate (3×30 mL), dried (MgSO$_4$), filtered, concentrated, and chromatographed on a 10 cm tall×26 mm diameter silica gel column eluting with 40% ethyl acetate in hexane to afford 6 (832 mg, 84%).

F. (5Z)-(9S,11S)-13-(t-Butyldiphenylsiloxy)-11-fluoro-9-hydroxy-14,15,16,17,18,19,20-heptanor-5-prostenoic acid isopropyl ester (7)

To a suspension of (4-carboxybutyl)triphenylphosphonium bromide (2.05 g, 4.63 mmol) in tetrahydrofuran (17 mL) at 0° C. (bath temperature) was added a 1 M solution of potassium t-butoxide in tetrahydrofuran (9.6 mL, 9.6 mmol). After 15 min, a solution of 6 (832 mg, 2.01 mmol) in tetrahydrofuran (10 mL) was added. After 90 min, saturated ammonium chloride (25 mL) was added, the mixture was extracted with ethyl acetate (3×35 mL), dried (magnesium sulfate), filtered, and concentrated. The residue was dissolved in acetone (18 mL), cooled to 0° C. (bath temperature), and DBU (1.83 g, 12.1 mmol) was added. After 20 min, isopropyl iodide (2.05 g, 12.1 mmol) was added, and the mixture was warmed to room temperature and stirred overnight. Saturated ammonium chloride (25 mL) was added, the mixture was extracted with ether (3×25 mL), dried (magnesium sulfate), filtered, concentrated, and chromatographed on a 19 cm tall×26 mm diameter silica gel column to afford 7 (781 mg, 68%).

G. (5Z)-(9S,11S)-13-(t-Butyldiphenylsiloxy)-11-fluoro-9-(tetrahydropyran-2-yloxy)-14,15,16,17,18,19,20-heptanor-5-prostenoic acid isopropyl ester (8)

To a mixture of 7 (780 mg, 1.44 mmol), methylene chloride (9 mL), and 3,4-dihydro-2H-pyran (184 mg, 2.20 mmol) at 0° C. (bath temperature) was added p-toluenesulfonic acid monohydrate (58 mg, 0.31 mmol). After 18 h, saturated sodium bicarbonate (20 mL) was added, the solution was extracted with methylene chloride (2×20 mL), dried (magnesium sulfate), filtered, concentrated, and chromatographed on a 15 cm tall×26 mm diameter silica gel column eluting with 20% ethyl acetate in hexane to afford 8 (687 mg, 76%).

H. (5Z)-(9S,11S)-11-Fluoro-13-hydroxy-9-(tetrahydropyran-2-yloxy)-14,15,16,17,18,19,20-heptanor-5-prostenoic acid isopropyl ester (9)

To a solution of 8 (683 mg, 1.09 mmol) in tetrahydrofuran (10 mL) was added a 1 M solution of tetra-n-butylammonium fluoride (TBAF) (1.5 mL, 1.5 mmol). After 18 h, saturated ammonium chloride (25 mL) was added, the solution was extracted with ethyl acetate (3×25 mL), dried (magnesium sulfate), filtered, concentrated, and chromatographed on a 16 cm tall×26 mm diameter silica gel column eluting with 40% ethyl acetate in hexane to afford 9 (356 mg, 85%).

I. (5Z)-(9S,11S)-11-Fluoro-13-oxo-9-(tetrahydropyran-2-yloxy)-14,15,16,17,18,19,20-heptanor-5-prostenoic acid isopropyl ester (10)

To a 2 M solution of oxalyl chloride in methylene chloride (0.54 mL, 1.08 mmol) in an additional 2 mL of methylene chloride at −78° C. (bath temperature) was added a solution of dimethyl sulfoxide (110 mg, 1.4 mmol) in methylene chloride (1 mL). After 15 min, a solution of 9 (287 mg, 0.74 mmol) in methylene chloride (4 mL) was added, and after an additional 20 min. triethylamine (360 mg, 3.6 mmol) was added. The solution was warmed to room temperature, saturated ammonium chloride (20 mL) was added, the mixture was extracted with methylene chloride (2×20 mL), dried (magnesium sulfate), filtered, concentrated, and chromatographed on a 16 cm tall×26 mm diameter silica gel column eluting with 40% ethyl acetate in hexane to afford 10 (261 mg, 92%).

J. (5Z,13E)-(9S,11S)-16-(3-Chlorophenoxy)-11-fluoro-15-oxo-9-(tetrahydropyran-2-yloxy)-17,18,19,20-tetranor-5,13-prostadienoic acid isopropyl ester (11)

To a mixture of dimethyl [3-(3-chlorophenoxy)-2-oxopropyl]phosphonate (395 mg, 1.35 mmol), tetrahydrofuran (3 mL), and lithium chloride (58 mg, 1.38 mmol) at 0° C. (bath temperature) was added triethylamine (95 mg, 0.93 mmol). After 5 min, a solution of 10 (256 mg, 0.67 mmol) in tetrahydrofuran (5 mL) was added. After 5 d, saturated ammonium chloride (15 mL) was added, the solution was extracted with ethyl acetate (3×20 mL), dried (magnesium sulfate), filtered, concentrated, and chromatographed on a 14 cm tall×26 mm diameter silica gel column eluting with 20% ethyl acetate in hexane to afford 11 (200 mg, 54%).

K. (5Z,13E)-(9S,11S,15R)-16-(3-Chlorophenoxy)-11-fluoro-15-hydroxy-9-(tetrahydropyran-2-yloxy)-17,18,19,20-tetranor-5,13-prostadienoic acid isopropyl ester (12)

To a mixture of 11 (193 mg, 0.35 mmol), cerium trichloride heptahydrate (228 mg, 0.61 mmol), and methanol (4 mL) at 0° C. (bath temperature) was added sodium borohydride (24 mg, 0.63 mmol) in 3 portions. After 2 h, saturated ammonium chloride (20 mL) was added, the mixture was extracted with ethyl acetate (3×20 mL), dried (magnesium sulfate), filtered, concentrated, and chromatographed on a 16 cm tall×26 mm diameter silica gel column eluting with 40% ethyl acetate in hexane to afford 12 and the corresponding 15S diastereomer (184 mg combined, 95% yield).

L. (5Z,13E)-(9S,11S,15R)-16-(3-Chlorophenoxy)-9,15-dihydroxy-11fluoro-17,18,19,20-tetranor-5,13-prostadienoic acid isopropyl ester (III)

To a mixture of 12 and the corresponding 15S diastereomer(180 mg, 0.32 mmol), isopropanol (4 mL), and water (1 mL) was added a solution of 12 M HCl (1 mL). After 1 h, saturated sodium bicarbonate (15 mL) was added, the mixture was extracted with ethyl acetate (3×20 mL), dried (magnesium sulfate), filtered, concentrated, and chromatographed on an 18 cm tall×26 mm diameter silica gel column eluting with 40% ethyl acetate in hexane to afford III (29.6 mg, 20%) as well as a mixture of III with the corresponding 15S diastereomer (96.1 mg, 64%). $^{13}$C NMR (CDCl$_3$) δ173.36 (C), 159.24 (C), 134.90 (C), 131.29 (CH), 130.56 (d,J=8 Hz, CH), 130.25 (CH), 130.08 (CH), 128.88 (CH), 121.37 (CH), 115.11 (CH), 113.15 (CH), 96.62 (d,J=176 Hz, CH), 72.03 (CH$_2$), 71.49 (CH), 70.79 (CH), 67.67 (CH), 50.71 (d,J=18 Hz, CH), 47.29 (CH), 42.76 (d,J=23 Hz, CH$_2$), 33.96 (CH$_2$), 26.66(CH$_2$), 24.80(CH$_2$), 24.58(CH$_2$), 21.81 (CH$_3$). Ms, m/z calcd. for C$_{25}$H$_{34}$O$_5$FClNa [(M+Na)$^+$], 491; found, 491.

EXAMPLE 2

Synthesis of IV

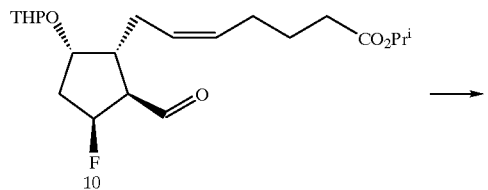

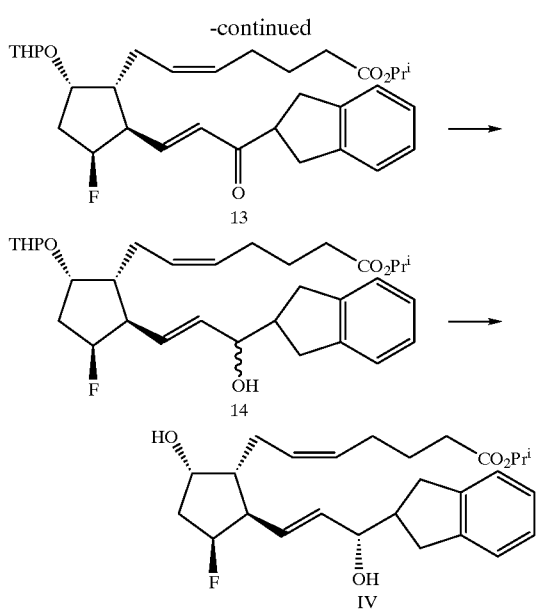

A. (5Z,13E)-(9S,11S)-11-Fluoro-15-(2-indanyl)-15-oxo-9-(tetrahydropyran-2-yloxy)-16,17,18,19,20-pentanor-5,13-prostadienoic acid isopropyl ester (13)

To a solution of lithium chloride (107 mg, 2.54 mmol), triethylamine (116 mg, 1.15 mmol), and dimethyl 2-oxo-2-(2-indanyl)ethylphosphonate (420 mg, 1.57 mmol) in THF (4 mL) at 0° C. (bath temperature) was added a solution of aldehyde 10 (300 mg, 0.78 mmol). The reaction was warmed to room temperature and stirred overnight. Saturated ammonium chloride (10 mL) was added, the mixture was extracted with ethyl acetate (3×10 mL), dried (magnesium sulfate), filtered, concentrated, and chromatographed on a 16 cm tall×26 mm diameter silica gel column eluting with 20% ethyl acetate in hexane to afford 13 (351 mg, 85%).

B. (5Z,13E)-(9S,11S,15RS)-11-Fluoro-15-hydroxy-15-(2indanyl)-9-(tetrahydropyran-2-yloxy)-16,17,18,19,20-pentanor-5,13-prostadienoic acid isopropyl ester (14)

To a mixture of 13 (340 mg, 0.64 mmol), methanol (10 mL), and cerium trichloride heptahydrate (620 mg, 1.66 mmol) at 0° C. (bath temperature) was added sodium borohydride (40 mg, 1.05 mmol) in 3 portions. After 2.5 h saturated potassium dihydrogen phosphate (10 mL) and water (10 mL) were added, the mixture was extracted with ethyl acetate (3×20 mL), dried (magnesium sulfate), filtered, and concentrated to afford 14 (340 mg, 100%).

C. (5Z,13E)-(9,S11,S15S)-9,15-Dihydroxy-11-fluoro-15-(2-indanyl)-16,17,18,19,20-pentanor-5,13-prostadienoic acid isopropyl ester (IV)

To a solution of 14 (340 mg, 0.64 mmol) in isopropanol (12 mL) was added a solution of 12 M HCl (1.1 mL). After 1 h 2 M sodium hydroxide (10 mL) was added, the layers were separated, the aqueous phase was extracted with ethyl acetate (2×15 mL), the combined organic layers were dried (magnesium sulfate), filtered, concentrated, and chromatographed on a 27 cm tall×26 mm diameter silica gel column eluting with 40% ethyl acetate in hexane to afford IV (53 mg, 19%), as well as the corresponding 15R diastereomer (76 mg, 27%). $^{13}$C NMR (CDCl$_3$) δ173.35 (C), 142.92 (C), 142.74 (C), 135.24 (CH), 130.02 (CH), 129.10 (d,J=9 Hz, CH), 128.93 (CH), 126.23 (CH), 126.16 (CH), 124.52 (CH), 124.32 (CH), 96.73 (d,J=174 Hz, CH), 76.42 (CH), 71.43 (CH), 67.68 (CH), 50.65 (d,J=18 Hz, CH), 47.35 (CH), 45.08 (CH), 42.79 (d,J=22 Hz, CH$_2$) 35.61 (CH$_2$), 35.46 (CH$_2$), 34.00 (CH$_2$), 26.69 (CH$_2$), 24.84 (CH$_2$), 24.62 (CH$_2$), 21.82 (CH$_3$). MS, m/z calcd. for C$_{27}$H$_{37}$O$_4$FNa [(M+Na)$^+$], 467; found, 467.

EXAMPLE 3

Synthesis of V

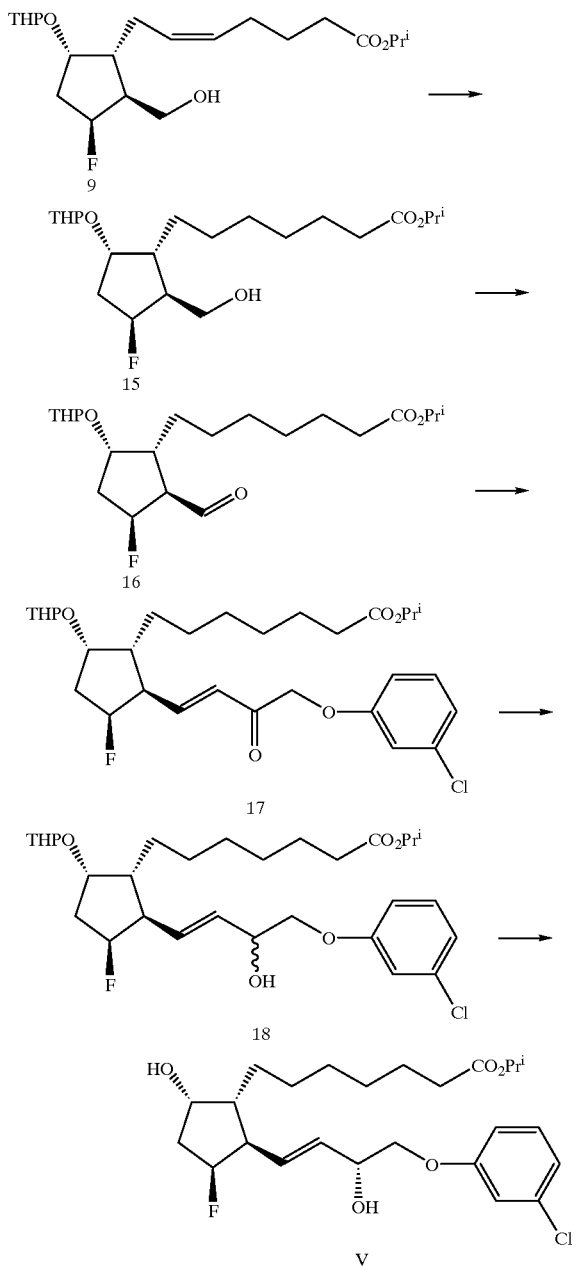

A. (9S,11S)-11-Fluoro-13-hydroxy-9-(tetrahydropyran-2-yloxy)-14,15,16,17,18,19,20-heptanorprostanoic acid isopropyl ester (15)

A suspension of olefin 9 (439 mg, 1.14 mmol) and 10% w/w Pd/C (70 mg) in ethyl acetate (10 mL) was stirred under hydrogen (1 atm pressure) overnight. The mixture was filtered through Celite and concentrated to afford 15 (442 mg, 100%).

B. (9S,11S)-11-Fluoro-13-oxo-9-(tetrahydropyran-2-yloxy)-14,15,16,17,18,19,20-heptanorprostanoic acid isopropyl ester (16)

To a 2 M solution of oxalyl chloride (0.92 mL, 1.84 mmol) in an additional 3.5 mL of methylene chloride at −78° C. (bath temperature) was added a solution of dimethyl sulfoxide (220 mg, 2.8 mmol) in methylene chloride (0.5 mL). After 15 min, a solution of 15 (441 mg, 1.14 mmol) in methylene chloride (4 mL) was added. After an additional 30 min triethylamine (360 mg, 3.56 mmol) was added, the solution was warmed to room temperature, saturated ammonium chloride (20 mL) was added, the mixture was extracted with methylene chloride (3×20 mL), dried (magnesium sulfate), filtered, concentrated, and chromatographed on a 12 cm tall×26 mm diameter silica gel column eluting with 40% ethyl acetate in hexane to afford 16 (445 mg, 100%).

C. (13E)-(9S,11S)-6-(3-Chlorophenoxy)-11-fluoro-15-oxo-9-(tetrahydropyran-2-yloxy)-17,18,19,20-tetranor-13-prostenoic acid isopropyl ester (17)

To a solution of triethylamine (180 mg, 1.8 mmol), lithium chloride (102 mg, 2.43 mmol), and dimethyl [3-(3-chlorophenoxy)-2-oxopropyl]phosphonate (670 mg, 2.29 mmol) in THF (5 mL) at 0° C. (bath temperature) was added a solution of 16 (440 mg, 1.14 mmol) in THF (4 mL). After 1 h the reaction was warmed to room temperature and stirred overnight. Saturated ammonium chloride (15 mL) was added, the solution was extracted with ethyl acetate (3×20 mL), dried (magnesium sulfate), filtered, concentrated, and chromatographed on a 15 cm tall×26 mm diameter silica gel column eluting with 20% ethyl acetate in hexane to afford 17 (317 mg, 50%).

D. (13E)-(9S,11S,15RS)-16-(3-Chlorophenoxy)-11-fluoro-15-hydroxy-9-(tetrahydropyran-2-yloxy)-17,18,19,20-tetranor-13-prostenoic acid isopropyl ester (18)

To a solution of 17 (312 mg, 0.56 mmol) and cerium trichloride heptahydrate (540 mg, 1.45 mmol) in methanol (9 mL) at 0° C. (bath temperature) was added sodium borohydride (44 mg, 1.17 mmol) in four portions. After 1 h, saturated ammonium chloride (20 mL) was added, the mixture was extracted with ethyl acetate (3×20 mL), dried (magnesium sulfate), filtered, and concentrated to afford a crude oil containing 18 (315 mg, 100%), which was used in the next step without further purification.

E. (13E)-(9S,11S,15R)-16-(3-Chlorophenoxy)-9,15-dihydroxy-11-fluoro-17,18,19,20-tetranor-13-prostenoic acid isopropyl ester (V)

To mixture of the crude oil from above (315 mg), isopropanol (12 mL), and water (1 mL) was added 12 M HCl (1 mL). After 3 h saturated sodium bicarbonate (20 mL) was added, the solution was extracted with ethyl acetate (3×20 mL), dried (magnesium sulfate), filtered, concentrated, and chromatographed on a 19 cm tall×53 mm diameter silica gel column eluting with 1:1 hexane:ethyl acetate to afford V (48 mg, 18% yield from 17), as well as the corresponding 15S diastereomer (83 mg, 31%) and a mixture of the two diastereomers (35 mg, 13%). $^{13}$C NMR (CDCl$_3$) δ173.53 (C), 159.28 (C), 134.88 (C), 131.23 (CH), 130.66 (d,J=9 Hz, CH), 121.34 (CH), 115.15 (CH), 113.14 (CH), 96.71 (d, J=175 Hz, CH), 72.11 (CH$_2$), 71.53 (d,J=2 Hz, CH), 70.78 (CH), 67.48 (CH), 50.93 (d, J=18 Hz, CH), 47.07 (CH), 43.06 (d,J=22 Hz, CH$_2$), 34.57 (CH$_2$), 29.36 (CH$_2$), 28,84 (CH$_2$), 27.67 (CH$_2$), 26.30 (CH$_2$), 24.69 (CH$_2$), 21.84 (CH$_3$). MS, m/z calcd. for C$_{25}$H$_{36}$O$_5$FClNa [(M+Na)$^+$], 493; found, 493.

EXAMPLE 4

Synthesis of VI

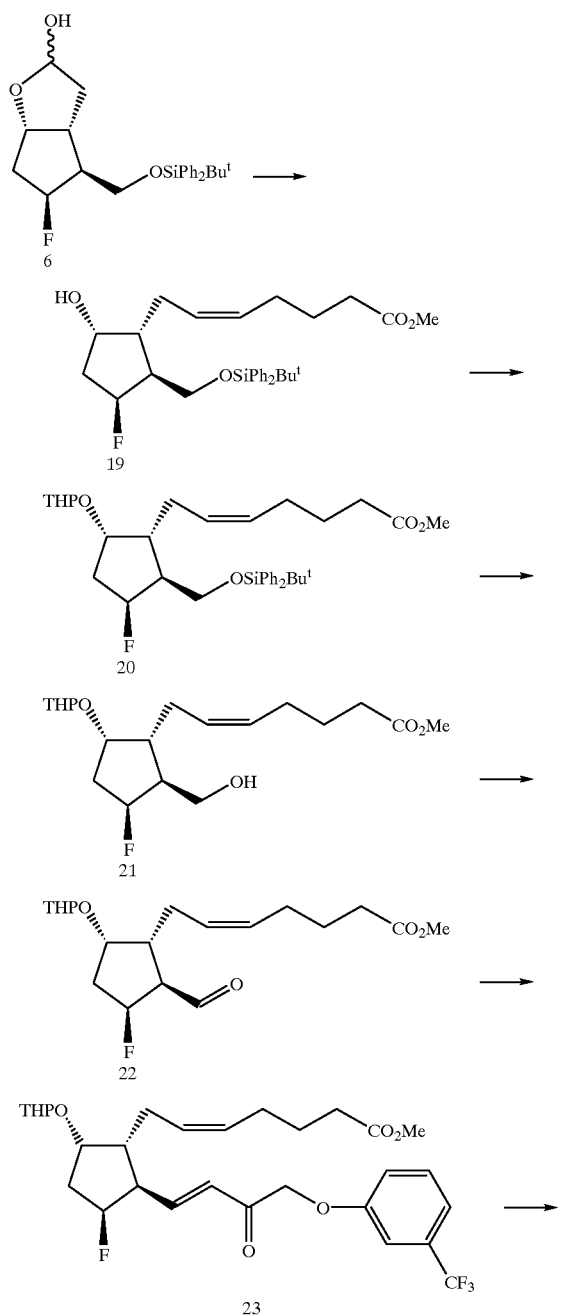

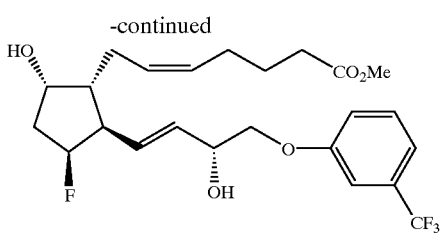

-continued

VI

A. (5Z)-(9S,11S)-13-(t-Butyldiphenylsiloxy)-11-fluoro-9-hydroxy-14,15,16,17,18,19,20-heptanor-5-prostenoic acid methyl ester (19)

To a solution of (4-carboxybutyl)triphenylphosphonium bromide (2.2 g, 5.0 mmol) in a mixture of dimethyl sulfoxide (40 mL) and THF (40 mL) at 0° C. (bath temperature) was added a 1 M solution of potassium t-butoxide in THF (10.5 mL, 10.5 mmol). After 15 min a solution of lactol 6 (1.0 g, 2.6 mmol) in THF (10 mL) was added, and the reaction was warmed to room temperature and was stirred overnight. The mixture was poured into saturated citric acid, extracted with ethyl acetate, dried (magnesium sulfate), filtered, and concentrated to afford a crude oil. This oil was dissolved in acetone (20 mL), DBU (1.5 g, 10 mmol) and methyl iodide (1.4 g, 10 mmol) were added, and the reaction was stirred overnight. The solution was concentrated, added to saturated citric acid, extracted with ethyl acetate, dried (magnesium sulfate), concentrated, and chromatographed on a silica gel column eluting with 7:3 hexane:ethyl acetate to afford 19 (580 mg, 44%).

B. (5Z)-(9S,11S)-13-(t-Butyldiphenylsiloxy)-11-fluoro-9-(tetrahydropyran-3-yloxy)-14,15,16,17,18,19,20-heptanor-5-prostenoic acid methyl ester (20)

To a solution of 19 (580 mg, 1.1 mmol) and 3,4-dihydro-2H-pyran (120 mg, 1.4 mmol) in methylene chloride (20 mL) at 0° C. (bath temperature) was added p-toluenesulfonic acid monohydrate (50 mg, 0.26 mmol). The reaction was warmed to room temperature, and after 3 h the solution was recooled to 0° C. (bath temperature) and additional 3,4-dihydro-2H-pyran (500 mg, 5.9 mmol) was added. After an additional 45 min the solution was added to saturated sodium bicarbonate, the phases were separated, the organic layer was dried (magnesium sulfate), filtered, concentrated, and chromatographed on a silica gel column eluting with 20% ethyl acetate in hexane to afford 20 (680 mg, 100%).

C. (5Z)-(9S,11S)-11-Fluoro-13-hydroxy-9-(tetrahydropyran-2-yloxy)-14,15,16,17,18,19,20-heptanor-5-prostenoic acid methyl ester (21)

To a solution of 20 (680 mg, 1.1 mmol) in THF (20 mL) was added a 1 M solution of TBAF in THF (1.5 mL, 1.5 mmol). After 16 h additional TBAF (0.5 mL, 0.5 mmol) was added. After 5 h more the solution was added to saturated ammonium chloride, water was added, the mixture was extracted with ethyl acetate, dried (magnesium sulfate), filtered, concentrated, and chromatographed to afford 21 (360 mg, 91%).

D. (5Z)-(9S,11S)-11-Fluoro-13-oxo-9-(tetrahydropyran-2-yloxy)-14,15,16,17,18,19,20-heptanor-5-prostenoic acid methyl ester (22)

To a solution of dimethyl sulfoxide (310 mg, 4.0 mmol) in methylene chloride (10 mL) at −78° C. (bath temperature)

was added a solution of oxalyl chloride (250 mg, 2.0 mmol) in methylene chloride (5 mL). After 15 min a solution of 21 (360 mg, 1.0 mmol) in methylene chloride (5 mL) was added. After an additional 15 min triethylamine (500 mg, 5.0 mmol) was added, the reaction was warmed to room temperature, added to saturated sodium bicarbonate, extracted with methylene chloride, dried (magnesium sulfate), filtered, concentrated, and chromatographed on a silica gel column eluting with 7:3 hexane:ethyl acetate to afford 22 (310 mg, 87%).

E. (5Z,13E)-(9S,11S)-11-Fluoro-15-oxo-9-(tetrahydropyran-2-yloxy)-16-[(3-trifluoromethyl)phenoxy]-17,18,19,20-tetranor-5,13-prostadienoic acid methyl ester (23)

To a solution of lithium chloride (130 mg, 3.0 mmol) and dimethyl [3-((3-trifluoromethyl)phenoxy)-2-oxopropyl]phosphonate (1.0 g, 3.0 mmol) in tetrahydrofuran (8 mL) was added triethylamine (250 mg, 2.5 mmol). After 10 min a solution of 22 (310 mg, 0.89 mmol) in THF (2 mL) was added, and the reaction was stirred for 3 d. The mixture was heated to 50° C. (bath temperature) for 3 h, cooled to room temperature, added to saturated sodium bicarbonate, extracted with ether, dried (magnesium sulfate), filtered, concentrated, and chromatographed on a silica gel column eluting with 7:3 ethyl acetate:hexane to afford 23 (100 mg, 20%).

F. (5Z,13E)-(9S,11S,15S)-9,15-Dihydroxy-11-fluoro-16-[(3-trifluoromethyl)phenoxy]-17,18,19,20-tetranor-5,13-prostadienoic acid methyl ester (VI)

To a solution of 23 (170 mg, 0.31 mmol) in methylene chloride (5 mL) at 0° C. (bath temperature) was added a solution of cerium trichloride heptahydrate (110 mg, 0.31 mmol) in methanol (3 mL, followed by sodium borohydride (12 mg, 0.31 mmol). A 2 h the solution was added to saturated ammonium chloride and was extracted with ethyl acetate, dried (magnesium sulfate), filtered, and concentrated to afford a crude oil. This oil was dissolved in a mixture of methanol (5 mL) and water (2 mL) and 12 M HCl (0.1 mL) was added. After 1 h the solution was added to saturated sodium bicarbonate and was extracted with ethyl acetate, dried (magnesium sulfate), filtered, concentrated, and chromatographed on a silica gel column eluting with 40% ethyl acetate in hexane to afford VI (20 mg, 14%). $^{13}$C NMR (CDCl$_3$) δ174.23, 158.66, 131.27, 130.70, 130.53, 130.03, 129.99, 128.92, 118.10, 117.91, 117.83, 111.56, 111.48, 98.35, 94.85, 72.07, 71.48, 70.82, 51.59, 50.92, 50.55, 47.30, 43.01, 42.57, 33.28, 30.90, 26.63, 24.69, 24.61.

EXAMPLE 5

Synthesis of VII

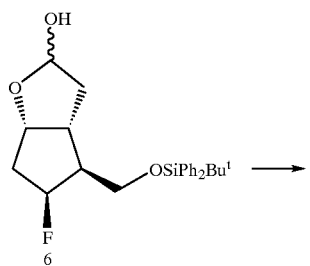

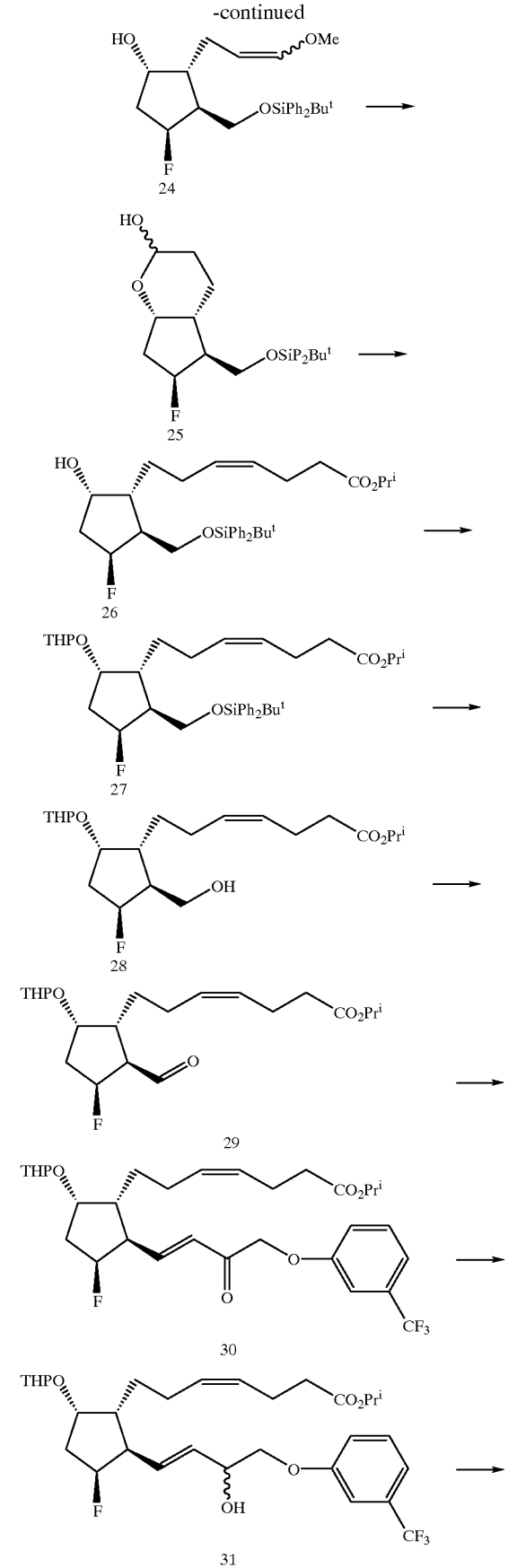

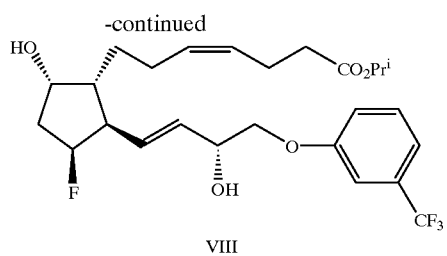

VIII (4Z,13E)-(9S,11S,15R)-9,15-Dihydroxy-11-fluoro-16-[(3-trifluoromethyl)phenoxyl]-17,18,19,20-tetranor-4,13-prostadienoic acid isopropyl ester (VII)

Wittig reaction of lactol 6 (see example 1) with $Ph_3P^+CH_2OMe\ Cl^-$ in the presence of potassium t-butoxide in THF affords enol ether 24. Hydrolysis of 24 to lactol 25 is effected by p-toluenesulfonic acid in THF/water. Wittig reaction of 25 with $Ph_3P^+(CH_2)_3CO_2H\ Br^-$ in the presence of potassium t-butoxide in THF, followed by alkylation of an acetone solution of the resultant carboxylic acid with isopropyl iodide in the presence of DBU yields cis-$\Delta^4$ olefin 26. Protection of the hydroxyl at carbon 9 as a THP ether gives 27, desilylation of which with TBAF affords alcohol 28. Oxidation to the aldehyde 29 is achieved under Swern conditions (DMSO/oxalyl chloride), followed by Homer Emmons reaction with dimethyl [3-((3-trifluoromethyl)phenoxy)-2-oxopropyl]phosphonate (see example 4) provides enone 30. Reduction of the ketone by $NaBH_4/CeCl_3$ in methanol yields ally alcohol 31 as a mixture of diastereomers, which is deprotected by aqueous methanolic HCl and purified to afford VII.

EXAMPLE 6

Synthesis of VIII

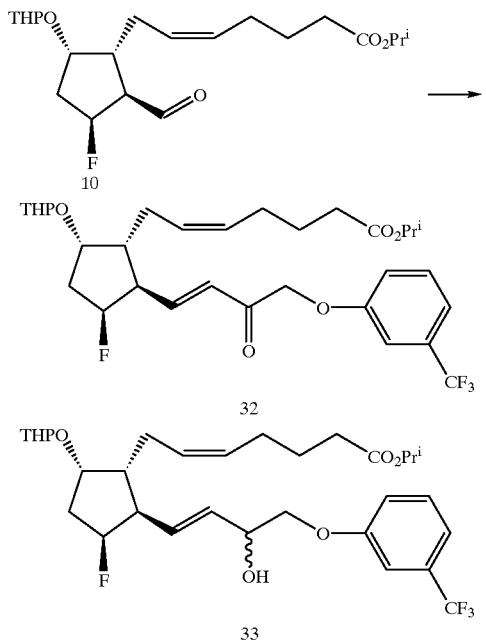

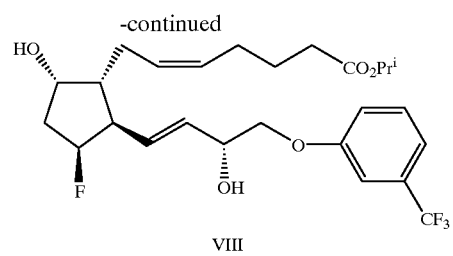

VIII (5Z,13E)-(9S,11S,15R)-9,15-Dihydroxy-11-fluoro-16-[(3-trifluoromethyl)phenoxy]-17,18,19,20-tetranor-5,13-prostadienoic acid isopropyl ester (VIII)

Homer-Emmons reaction of aldehyde 10 with dimethyl [3-((3-trifluoromethyl)phenoxy)-2-oxopropyl]phosphonate (prepared in a manner analogous to that described in U.S. Pat. No. 5,665,773 for dimethyl (2-oxo-3-(3-chlorophenoxy)propyl)phosphonate, which patent is incorporated herein by this reference) in THF in the presence of LiCl and $NEt_3$ affords enone 32. Reduction of 32 with $NaBH_4/CeCl_3$ in methanol provides allyl alcohol 33 as a mixture of diastereomers. Deprotection of 33 by methanolic aqueous HCl followed by chromatographic purification yields VIII.

EXAMPLE 7

Synthesis of IX

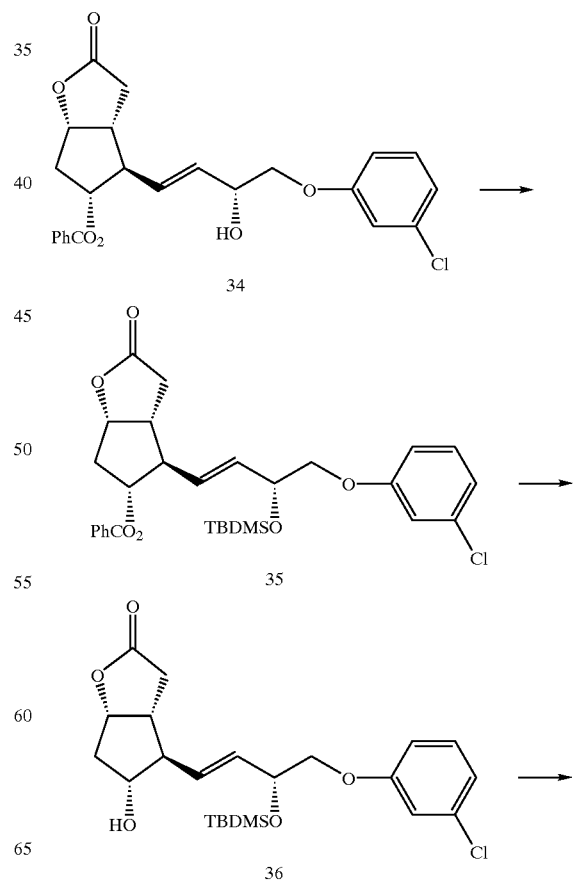

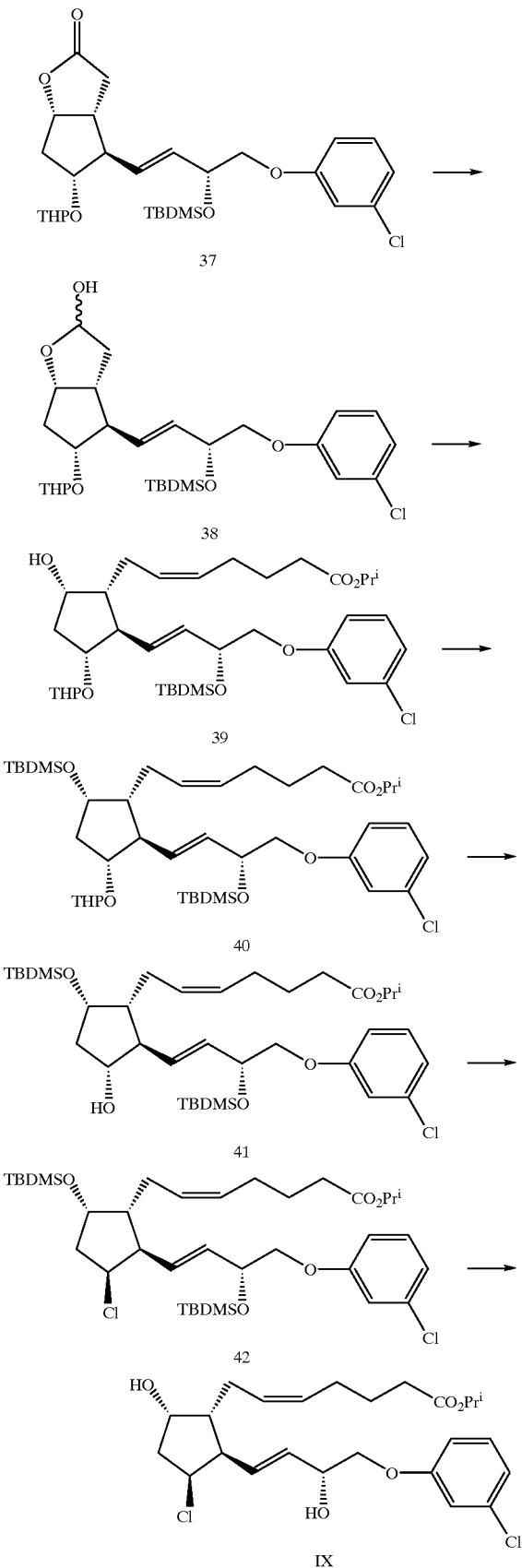

A. [3aR,4R(1E,3R),5R,6aS]-5-Benzoyloxy-4-[4-(3-chlorophenxoy)-3-(t-butyldimethylsiloxy)butenyl]-hexahydro-2H-cyclopenta[b]furan-2-one (35)

To a solution of [3aR,4R(1E,3R),5R,6aS]-5-Benzoyloxy-4-[4-(3-chlorophenxoy)-3-hydroxybutenyl]-hexahydro-2H-cyclopenta[b]furan-2-one (34; for preparation, see U.S. Pat. No. 5,665,773) (599 mg, 1.36 mmol), imidazole (380 mg, 2.52 mmol), and 4-(dimethylamino)pyridine (DMAP; 33 mg, 0.27 mmol) in $CH_2Cl_2$ (15 mL) was added t-butyldimethylsilyl chloride (380 mg, 2.52 mmol). After 1 h, saturated brine (10 mL) was added, the layers were separated, the aqueous phase was extracted with $CH_2Cl_2$ (2×15 mL), the combined organic layers were dried ($MgSO_4$), filtered, and concentrated, and the residue was flash chromatographed on a 16 cm tall×41 mm diameter silica gel column eluting with 30% ethyl acetate in hexane to afford 35 (631 mg, 83%). $^{13}$C NMR ($CDCl_3$) δ176.31 (C), 166.04 (C), 159.47 (C), 134.93 (C), 133.38 (CH), 132.89 (CH), 130.28 (CH), 129.87 (CH), 129.70 (CH), 129.58 (C), 128.54 (CH), 121.10 (CH), 114.93 (CH), 113.05 (CH), 83.14 (CH), 78.90 (CH), 72.27 ($CH_2$), 71.24 (CH), 53.81 (CH), 42.66 (CH), 37.65 ($CH_2$), 34.73 ($CH_2$), 25.83 ($CH_3$), 18.32 (C). MS, m/z calcd. for $C_{30}H_{37}O_6ClSiNa$ [(M+Na)$^+$], 579.194360; found, 579.19433.

B. [3aR,4R(1E,3R),5R,6aS]-4-[4-(3-Chlorophenxoy)-3-(t-butyldimethylsiloxy)butenyl]-5-hydroxy-hexahydro-2H-cyclopenta[b]furan-2-one (36)

To a solution of 35 (630 mg, 1.13 mmol) in methanol (25 mL) was added $K_2CO_3$ (160 mg, 1.16 mmol). After 3 h, saturated $NH_4Cl$ (25 mL) and saturated brine (30 mL) were added, the mixture was extracted with ethyl acetate (4×30 mL), dried ($MgSO_4$), filtered, and concentrated, and the residue was flash chromatographed on a 28 cm tall×26 mm diameter silica gel column eluting with 40% ethyl acetate in hexane to afford 36 (405 mg, 79%). $^{13}$C NMR ($CDCl_3$) δ176.71 (C), 159.50 (C), 134.96 (C), 132.75 (CH), 130.55 (CH), 130.31 (CH), 121.15 (CH), 114.98 (CH), 113.10 (CH), 82.71 (CH), 76.97 (CH), 72.39 ($CH_2$), 71.28 (CH), 56.25 (CH), 42.74 (CH), 40.16 ($CH_2$), 34.45 ($CH_2$), 25.86 ($CH_3$), 18.39 (C). MS, m/z calcd. for $C_{23}H_{34}O_5ClSi$ [(M+H)$^+$], 453.186883; found, 453.18689.

C. [3aR,4R(1E,3R),5R,6aS]-4-[4-(3-Chlorophenxoy)-3-(t-butyldimethylsiloxy)butenyl]-5-(tetrahydropyran-2-yloxy)-hexahydro-2H-cyclopenta[b]furan-2-one (37)

To a solution of 36 (400 mg, 0.883 mmol) and 3,4-dihydro-2H-pyran (DHP; 100 mg, 1.19 mmol) in $CH_2Cl_2$ (12 mL) at 0° C. (bath temperature) was added p-toluenesulfonic acid monohydrate (TsOH; 37 mg, 0.19 mmol). After 35 min, $NEt_3$ (0.1 mL) was added, the solution was concentrated, and the residue was chromatographed on a 22 cm tall×26 mm diameter silica gel column eluting with 30% ethyl acetate in hexane to afford 37 (475 mg, 100%) ($R_f$=0.67, 40% ethyl acetate in hexane eluent). MS, m/z calcd. for $C_{28}H_{42}O_6ClSi$ [(M+H)$^+$], 537.24440; found, 537.24438.

D. [3aR,4R(1E,3R),5R,6aS]-4-[4-(3-Chlorophenxoy)-3-(t-butyldimethylsiloxy)butenyl]-5-(tetrahydropyran-2-yloxy)-hexahydro-2H-cyclopenta[b]furan-2-ol (38)

To a −78° C. (bath temperature) solution of 37 (470 mg, 0.88 mmol) in toluene (8 mL) was added 1.1 mL of a 1.5 M solution of diisobutylaluminum hydride (DIBAL) in toluene (1.6 mmol). After 1 h, methanol (2 mL) and saturated NH$_4$Cl (4 mL) were added, and the solution was warmed to room temperature. A saturated solution of sodium potassium tartrate (15 mL) was added and the mixture was stirred for 10 minutes to break the emulsion. The layers were separated, the aqueous phase was extracted with ethyl acetate (2×15 mL), the combined organic layers were dried (MgSO$_4$), filtered, and concentrated to afford 38 (456 mg, 96%) (R$_f$=0.45, 40% ethyl acetate in hexane eluent).

E. (5Z,13E)-(9S,11R,15R,)-15-(t-Butyldimethylsiloxy)-16-(3-chlorophenoxy)-9-hydroxy-11-(tetrahydropyran-2-yloxy)-17,18,19,20-tetranor-5,13-prostadienoic acid isopropyl ester (39)

To a suspension of Ph$_3$P$^+$(CH$_2$)$_4$CO$_2$H Br$^-$(760 mg, 1.72 mmol) in THF (5 mL) at 0° C. (bath temperature) was added dropwise a 1 M solution of potassium t-butoxide (t-BuOK) in THF (4.2 mL, 4.2 mmol). After 15 minutes, a solution of 38 (450 mg) in THF (7 mL) was added dropwise. After an additional 90 minutes, saturated NH$_4$Cl (25 mL) was added, the solution was extracted with ethyl acetate (4×25 mL), dried (Na$_2$SO$_4$), decanted, and concentrated to afford the crude Wittig product as an oil. This oil was dissolved in acetone (17 mL), the solution was cooled to 0° C. (bath temperature), and 1,8-diazabicyclo[5.4.0]undec-7-ene (DBU) was added (760 mg, 4.98 mmol). After 20 min, isopropyl iodide (850 mg, 5.00 mmol) was added, and the reaction was warmed to room temperature and stirred overnight. Saturated NH$_4$Cl (20 mL) was added, the solution was extracted with ethyl acetate (3×25 mL), dried (MgSO$_4$), filtered, and concentrated. The residue was flash chromatographed on a 20 cm tall×26 mm diameter silica gel column eluting with 40% ethyl acetate in hexane to provide 39 (350 mg, 63%). MS, m/z calcd. for C$_{36}$H$_{57}$O$_7$ClSiNa [(M+Na)$^+$], 687.346458; found, 687.34643.

F. (5Z,13E)-(9S,11R,15R)-9,15-Bis(t-Butyldimethylsiloxy)-16-(3-chlorophenoxy)-11-(tetrahydropyran-2-yloxy)-17,18,19,20-tetranor-5,13-prostadienoic acid isopropyl ester (40)

To a solution of 39 (345 mg, 0.52 mmol), DMAP (15.5 mg, 0.13 mmol), and imidazole (77.3 mg, 1.14 mmol) in CH$_2$Cl$_2$ (6 mL) was added t-butyldimethylsilyl chloride (140 mg, 0.93 mmol). After stirring overnight, the reaction was not yet complete, so portions of NEt$_3$ (120 mg, 1.2 mmol) and t-butyldimethylsilyl trifluoromethanesulfonate (TBSOTf) (260 mg, 1.0 mmol) were added sequentially. After 40 minutes, saturated NaHCO$_3$ (5 mL) was added, the phases were separated, the aqueous layer was extracted with CH$_2$Cl$_2$ (3×5 mL), the combined organic layers were dried (MgSO$_4$), filtered, and concentrated, and the residue was flash chromatographed on a 15 cm tall×26 mm diameter silica gel column eluting with 20% ethyl acetate in hexane to afford 40 (372 mg, 92%). MS, m/z calcd. for C$_{42}$H$_{71}$O$_7$ClSiNa [(M+Na)$^+$]; 801.434301; found, 801.43432.

G. (5Z,13E)-(9S,11R,15R)-9,15-Bis(t-Butyldimethylsiloxy)-16-(3-chlorophenoxy)11-hydroxy-17,18,19,20-tetranor-5,13-prostadienoic acid isopropyl ester (41)

To a solution of 40 (367 mg, 0.47 mmol) in diethyl ether (11 mL) was added MgBr$_2$ (261 mg, 1.42 mmol). After 7 h, NEt$_3$ (0.5 mL) and saturated NaHCO$_3$ (15 mL) were sequentially added, the mixture was extracted with ethyl acetate (3×20 mL), dried (MgSO$_4$), filtered, and concentrated. The residue was flash chromatographed on an 8 mm tall×15 mm diameter silica gel column eluting with 10% ethyl acetate in hexane to afford 41 (101 mg, 28%) as well as recovered 40 (121 mg, 37%). Re-subjection of the isolated starting material to the reaction conditions afforded an additional quantity of 41 (29 mg; total=130 mg=36% yield). $^{13}$C NMR (CDCl$_3$) δ173.05 (C), 159.60 (C), 134.79 (C), 133.95 (CH), 130.13 (CH), 129.25 (CH), 120.81 (CH), 114.93 (CH), 112.95 (CH), 78.77 (CH), 74.62 (CH), 72.61 (CH$_2$), 71.62 (CH$_2$), 67.94 (CH$_2$), 67.36 (CH), 56.77 (CH), 51.49 (CH), 43.38 (CH$_2$), 34.13 (CH$_2$), 26.76 (CH$_2$), 26.17 (CH$_2$), 25.83 (CH$_3$), 25.58 (CH$_2$), 24.82 (CH$_2$), 21.83 (CH$_3$), 18.29 (C), 17.97 (C), −4.40 (CH$_3$), −4.55 (CH$_3$), −4.67 (CH$_3$), −5.09 (CH$_3$). MS, m/z calcd. for C$_{37}$H$_{63}$O$_6$ClSi$_2$Na [(M+Na)$^+$], 717; found, 717.

(5Z,13E)-(9S,11S,15R)-9,15-Bis(t-Butyldimethylsiloxy)-11-chloro-16-(3-chlorophenoxy)-17,18,19,20-tetranor-5,13-prostadienoic acid isopropyl ester (42)

To a solution of 41 (144 mg, 0.21 mmol) and NEt$_3$ (65 mg, 0.65 mmol) in CH$_2$Cl$_2$ (3 mL) at 0° C. (bath temperature) was added CH$_3$SO$_2$Cl (59 mg, 0.52 mmol). After 30 min, the mixture was brought to room temperature, and after 50 additional minutes the reaction was quenched by the addition of saturated NaHCO$_3$ (5 mL). The layers were separated, the aqueous phase was extracted with CH$_2$Cl$_2$ (2×5 mL), and the combined organic layers were dried (MgSO$_4$), filtered, and concentrated to afford an oil. This oil was dissolved in toluene (3.5 mL), Bu$_4$NCl was added (466 mg, 1.68 mmol), and the solution was heated to 70° C. (bath temperature). After 5 h, the reaction was cooled to room temperature, saturated brine was added (10 mL), the mixture was extracted with ethyl acetate (4×10 mL), and the combined organic layers were dried (MgSO$_4$), filtered, and concentrated. The residue was flash chromatographed on a 19 cm tall×10 mm diameter silica gel column eluting with 40% ethyl acetate in hexane to afford 42 along with some amount of an elimination by-product and some partially de-silylated material (119 mg, 79% nominal yield calculated as 42).

(5Z,13E)-(9S,11S,15R)-11-Chloro-16-(3-chlorophenoxy)-9,15-dihydroxy-17,18,19,20-tetranor-5,13-prostadienoic acid isopropyl ester (IX)

To a solution of the above-obtained sample of impure 42 (119 mg) in THF (8 mL) was added a 1 M solution of tetra-n-butylammonium fluoride (TBAF) in THF (1.0 mL, 1.0 mmol). After 2.5 hours, saturated NH$_4$Cl was added (10 mL), the mixture was extracted with ethyl acetate (3×15 mL), dried (MgSO$_4$), filtered, and concentrated. The residue was flash chromatographed on a 27 cm tall×10 mm diameter silica gel column eluting with 2:1 hexane:ethyl acetate to afford IX (19.9 mg, 25% nominal yield from 42). $^{13}$C NMR (CDCl$_3$) δ173.37 (C), 159.23 (C), 135.00 (C), 132.51 (CH), 131.13 (CH), 130.25 (CH), 130.19 (CH), 128.93 (CH), 121.36 (CH), 115.10 (CH), 113.14 (CH), 71.98 (CH$_2$), 71.32 (CH), 70.67 (CH), 67.67 (CH), 64.21 (CH), 51.11 (CH), 46.94 (CH), 46.46 (CH$_2$), 33.98 (CH$_2$), 26.69 (CH$_2$), 24.76 (CH$_2$), 24.57 (CH$_2$), 21.80 (CH$_3$). MS, m/z calcd. for C$_{25}$H$_{35}$O$_5$Cl$_2$ [(M+H)$^+$], 485.18556; found, 485.18554.

EXAMPLE 8

Synthesis of X

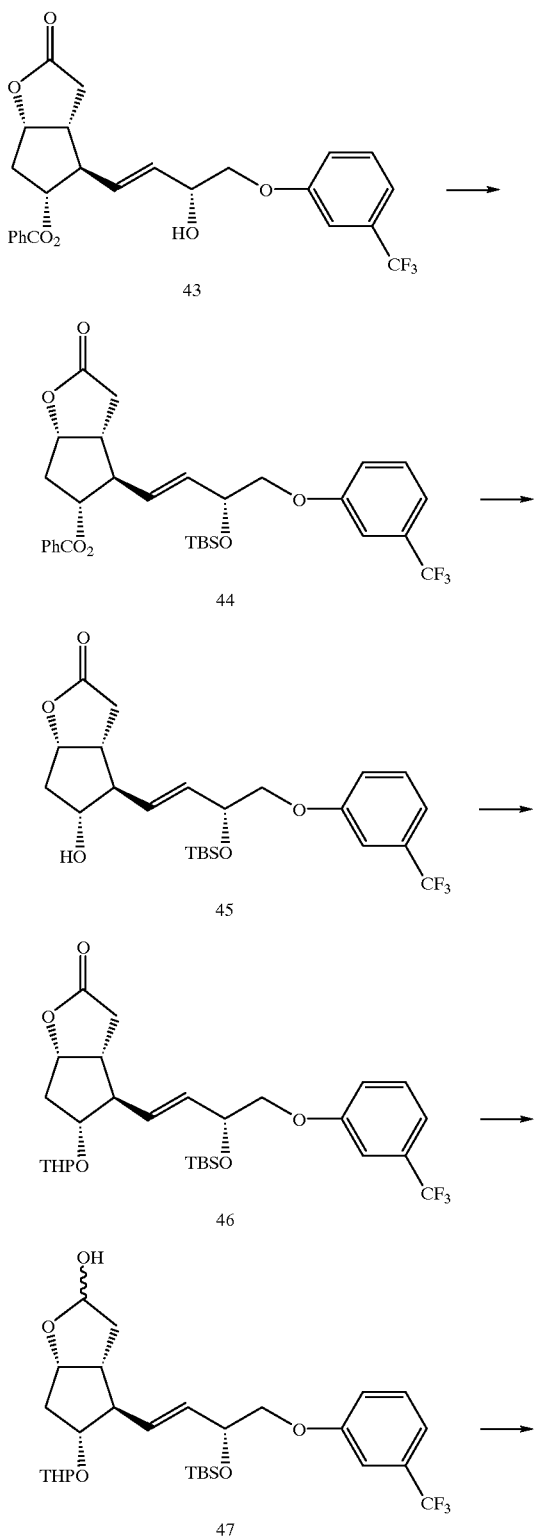

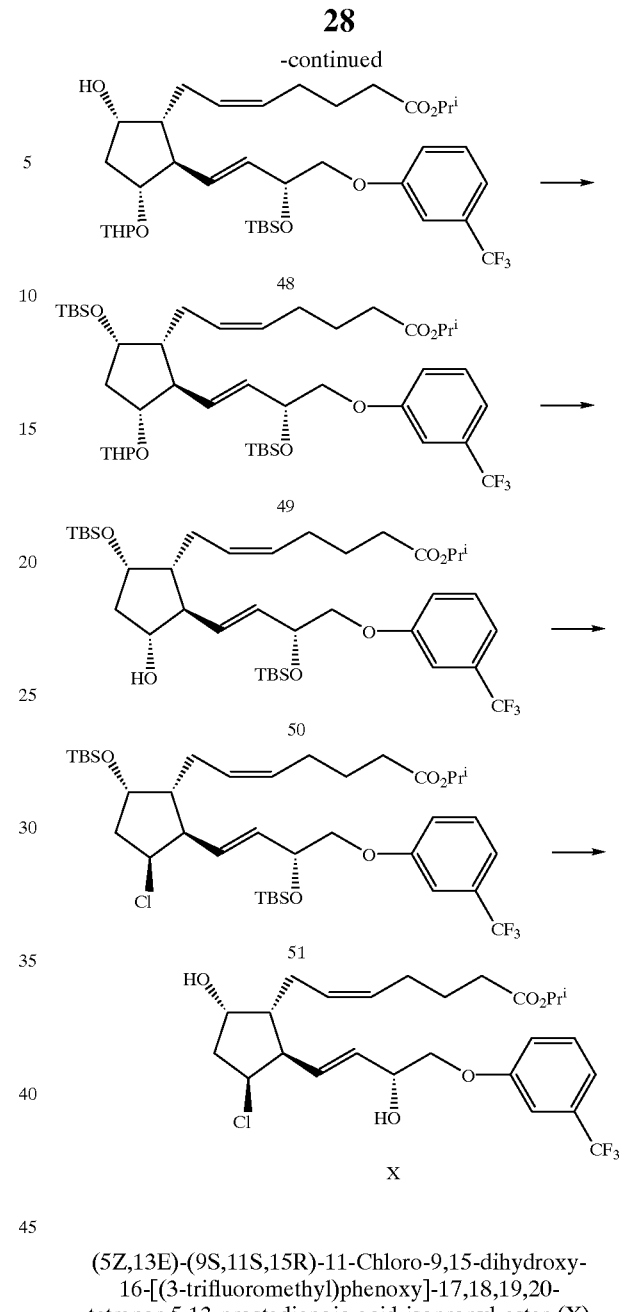

(5Z,13E)-(9S,11S,15R)-11-Chloro-9,15-dihydroxy-16-[(3-trifluoromethyl)phenoxy]-17,18,19,20-tetranor-5,13-prostadienoic acid isopropyl ester (X)

Silylation of allyl alcohol 43 (for preparation, see U.S. Pat. No. 4,321,275) with TBSOTf/NEt$_3$ in CH$_2$Cl$_2$ gives 44, which upon treatment with K$_2$CO$_3$ provides 45. Treatment of 45 with DHP and p-TsOH in CH$_2$Cl$_2$ affords THP ether 46, which is reduced with DIBAL in toluene at −78° C. to yield lactol 47. Wittig reaction of 47 with Ph$_3$P$^+$(CH$_2$)$_4$CO$_2$H Br$^−$ in THF in the presence of t-BuOK, followed by esterification of the resultant carboxylic acid with DBU/isopropyl iodide in acetone, provides hydroxyester 48. Silylation of 48 with TBSOTf/NEt$_3$ in CH$_2$Cl$_2$ gives 49, which is converted to alcohol 50 with MgBr$_2$ in diethyl ether. Chlorination to 51 is effected by treatment with PPh$_3$ and CCl$_4$ in acetonitrile. Desilylation upon treatment with TBAP in THF affords X.

EXAMPLE 9

Synthesis of XI

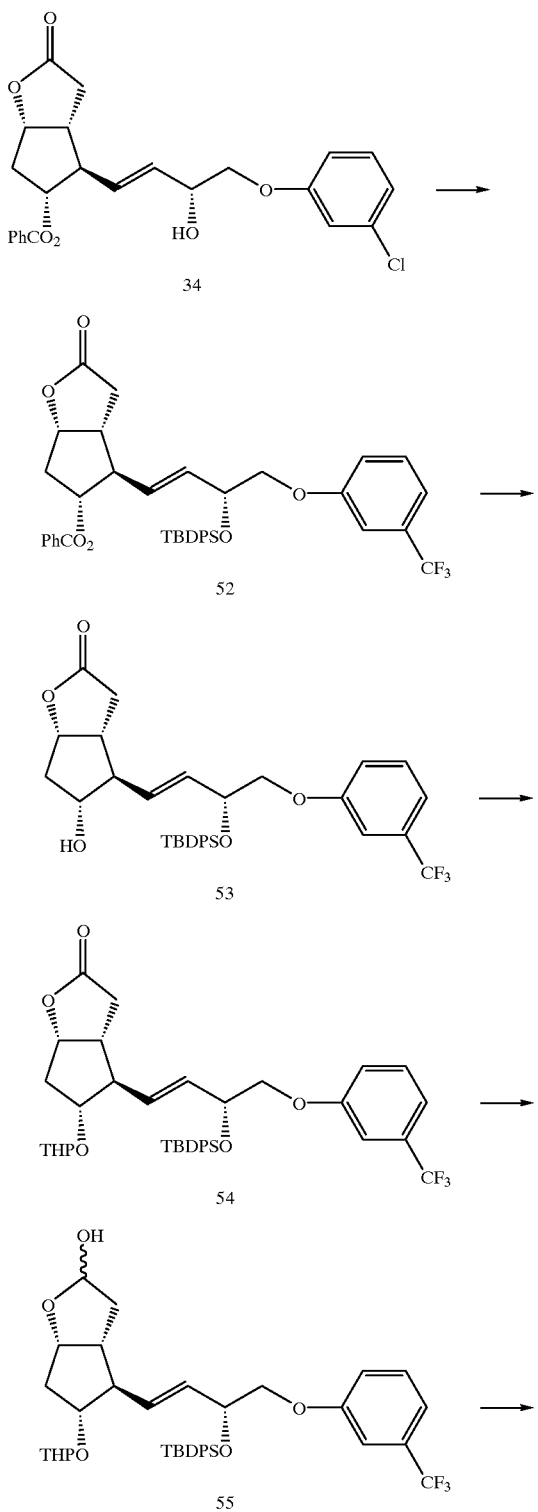

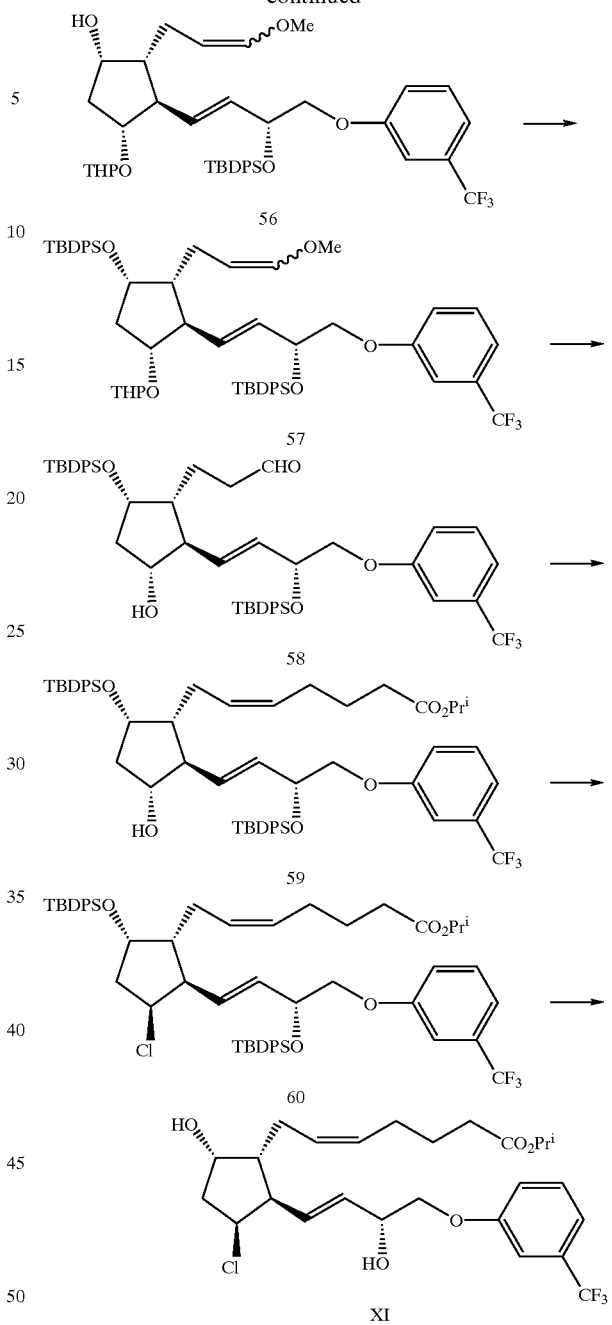

(4Z,13E)-(9S,11S,15R)-11-Chloro-16-(3-chlorophenoxy)-9,15-dihydroxy-17,18,19,20-tetranor-4,13-prostadienoic acid isopropyl ester (XI)

Treatment of a $CH_2Cl_2$ solution of 34, DMAP, and imidazole with t-butyldiphenylsilyl chloride (TBDPSCl) affords 52, which is debenzoylated with $K_2CO_3$ in methanol to yield 53. THP ether formation is effected by treatment with DHP and p-TsOH in $CH_2Cl_2$ to provide 54, which is reduced to lactol 55 by DIBAL in toluene at −78° C. Wittig reaction with $Ph_3P^+CH_2OCH_3$ $Cl^-$ in THF in the presence of t-BuOK affords enol ether 56, which is silylated by TBDP-SCl in DMF in the presence of imidazole and DMAP to provide 57. Treatment of 57 with p-TsOH in hot THF/water affords hydroxyaldehyde 58. Wittig reaction of 58 with $Ph_3P^+(CH_2)_3CO_2H$ $Br^-$ in THF in the presence of t-BuOK, followed by esterification of the resultant carboxylic acid with DBU/isopropyl iodide in acetone, provides hydroxyester 59. Chlorination of 59 with $PPh_3$ and $CCl_4$ in acetonitrile affords 60, which is desilylated by TBAF in THF to yield XI.

The 11-halo substituted prostaglandins of the present invention may be formulated in various pharmaceutical compositions for administering to humans and other mammals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention can be administered as solutions, suspensions, or emulsions (dispersions) in an ophthalmically acceptable vehicle. As used herein, the term "ophthalmically acceptable vehicle" refers to any substance or combination of substances which are non-reactive with the compounds and suitable for administration to a patient. Solubilizers and stabilizers are deemed to be non-reactive. Preferred are aqueous vehicles suitable for topical application to the patient's eyes.

In forming compositions for topical administration, the compounds of the present invention are generally formulated as between about 0.00003 to about 0.5 percent by weight (wt %) solutions in water at a pH between 4.5 to 8.0, preferably between about 7.0 and 7.5. The compounds are preferably formulated as between about 0.0005 to about 0.03 wt % and, most preferably, between about 0.001 and about 0.01 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents, and viscosity building agents.
Antimicrobial Preservatives Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.
Co-Solvents Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; CREMOPHORE® EL (polyoxyl 35 castor oil) cyclodextrin; or other agents known to those skilled in the art. Such co-solvents are typically employed at a level between about 0.01% and about 2% by weight.
Viscosity Agents Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight.

Preferred formulations of the 11-halo prostaglandins of the present invention include the following Examples 10–15:

EXAMPLE 10

| Ingredient | Amount (wt %) |
|---|---|
| Compound VII | 0.005 |
| Phosphate Buffered Saline | 1.0 |
| Polysorbate 80 | 0.5 |
| Purified water | q.s. to 100% |

EXAMPLE 11

| Ingredient | Amount (wt %) |
|---|---|
| Compound VIII | 0.001 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| CREMOPHOR ® EL | 0.1 |
| Benzalkonium chloride | 0.01 |
| HCl and/or NaOH | pH 7.3–7.4 |
| Purified water | q.s. to 100% |

EXAMPLE 12

| Ingredient | Amount (wt %) |
|---|---|
| Compound IV | 0.1 |
| Phosphate Buffered Saline | 1.0 |
| Hydroxypropyl-β-cyclodextrin | 4.0 |
| Purified water | q.s. to 100% |

EXAMPLE 13

| Ingredient | Amount (wt %) |
|---|---|
| Compound XI | 0.005 |
| Phosphate Buffered Saline | 1.0 |
| Polysorbate 80 | 0.5 |
| Purified water | q.s. to 100% |

EXAMPLE 14

| Ingredient | Amount (wt %) |
|---|---|
| Compound IX | 0.005 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| CREMOPHOR ® EL | 0.1 |
| Benzalkonium chloride | 0.01 |
| HCl and/or NaOH | pH 7.3–7.4 |
| Purified water | q.s. to 100% |

EXAMPLE 15

| Ingredient | Amount (wt %) |
|---|---|
| Compound X | 0.1 |
| Phosphate Buffered Saline | 1.0 |
| Hydroxypropyl-β-cyclodextrin | 4.0 |
| Purified water | q.s. to 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma or ocular hypertension in a patient suffering therefrom, which comprises administering to the patient a pharmaceutically effective amount of a compound of formula I:

wherein:
$n=0$ or 2;
$R^1=CO_2R$, $CONR^4R^5$, $CH_2OR^6$, or $CH_2NR^7R^8$; where:
  R=H or cationic salt moiety, or $CO_2R$ forms an ophthalmically acceptable ester moiety;
  $R^4$, $R^5$=same or different=H or alkyl; $R^6$=H, acyl, or alkyl;
  $R^7$, $R^8$=same or different=H, acyl, or alkyl; with the proviso that if one of $R^7$, $R^8$=acyl, then the other=H or alkyl;
Q=halo;
one of $T^1$, $T^2$=H, and the other=$OR^3$; wherein $R^3$ is as defined below; or $T^1$ and $T^2$ together=O;
$R^2$, $R^3$=same or different=H, alkyl, or acyl;
- - - =single or non-cumulated double bond, with the provisos that a double bond between carbons 4 and 5 may not be of the trans configuration; and that a double bond between carbons 13 and 14 may not be of the cis configuration;
$X=(CH_2)_q$ or $(CH_2)_qO$; where q=1–6; and
Y=a phenyl ring optionally substituted with alkyl, halo, trihalomethyl, alkoxy, acyl, acyloxy, amino, alkylamino, acylamino, or hydroxy; or
$X—Y=(CH_2)_pY_1$; where p=0–6; and wherein:
$W=CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;
Z=H, alkyl, alkoxy, acyl, acyloxy, halo, trihalomethyl, amino, alkylamino, acylamino, or hydroxy; and
- - - =single or double bond.

2. The method of claim 1, wherein the compound is administered topically.

3. The method of claim 2, wherein the compound is administered as a solution, suspension, or emulsion.

4. The method of claim 2, wherein the concentration of the compound is between about 0.00003 to about 0.5 weight percent.

5. The method of claim 4, wherein the concentration of the compound is between about 0.0005 to about 0.03 weight percent.

6. The method of claim 5, wherein the concentration of the compound is between about 0.001 to about 0.01 weight percent.

7. The method of claim 4, wherein the compound is:

8. The method of claim 1, wherein the compound is of formula II:

wherein:
R=H; or $CO_2R$ forms an ophthalmically acceptable ester moiety;
- - - =single or non-cumulated double bond, with the provisos that a double bond between carbons 4 and 5 may not be of the trans configuration; and that a double bond between carbons 13 and 14 may not be of the cis configuration;
Q=Cl or F;

X=CH₂CH₂ or CH₂O; and

Y=phenyl, optionally substituted with halo or trihalomethyl; or

X—Y=(CH₂)_pY¹; where p=0; and

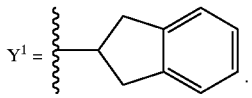

9. The method of claim 8, wherein:

CO₂R forms the ophthalmically acceptable ester moiety;

X=CH₂O; and

Y=substituted phenyl, where the substituent is selected from the group consisting of chloro and trifluoromethyl.

10. The method of claim 9, wherein the ophthalmically acceptable ester moiety is a C₂–C₄ alkyl ester.

11. The method of claim 10, wherein the compound is:

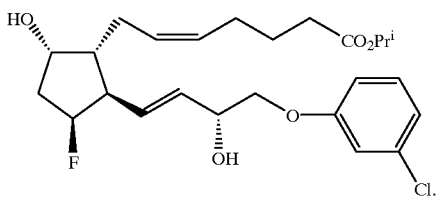

12. The method of claim 10, wherein the compound is:

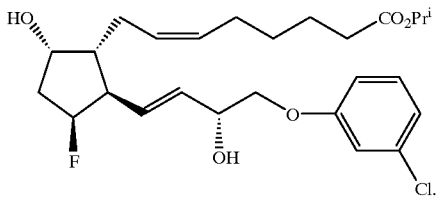

13. The method of claim 10, wherein the compound is:

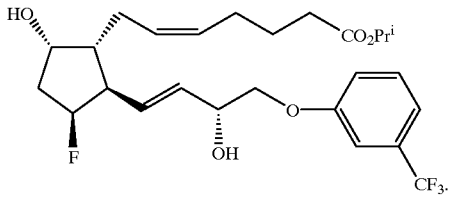

14. The method of claim 10, wherein the compound is:

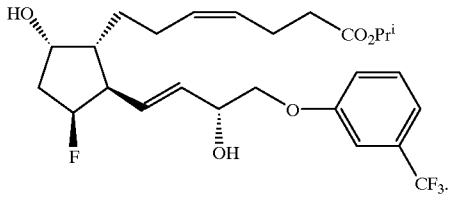

15. The method of claim 10, wherein the compound is:

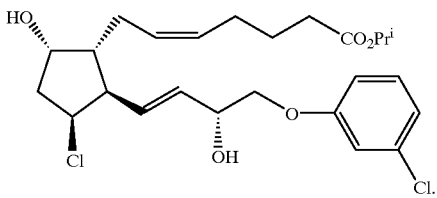

16. The method of claim 10, wherein the compound is:

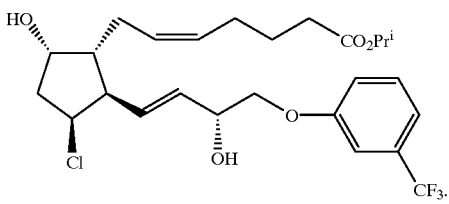

17. The method of claim 10, wherein the compound is:

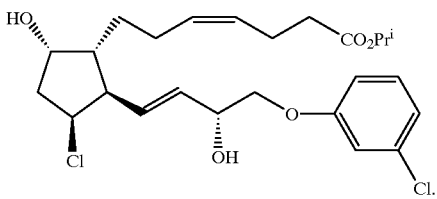

18. A compound of formula I:

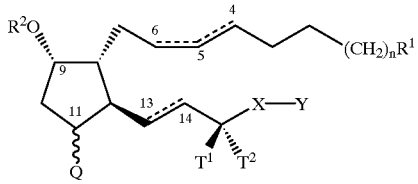

wherein:

n=0 or 2;

R¹=CO₂R, CONR⁴R⁵, CH₂OR⁶, or CH₂NR⁷R⁸; where R=H or cationic salt moiety, or CO₂R forms a pharmaceutically acceptable ester moiety; R⁴, R⁵=same or different=H or alkyl; R⁶=H, acyl, or alkyl; R⁷, R⁸=same or different=H, acyl, or alkyl; with the proviso that if one of R⁷, R⁸=acyl, then the other=H or alkyl;

Q=halo;

one of T¹, T²=H, and the other=OR³, where R³ is as defined below; or T¹ and T² together=O;

R², R³=same or different=H, alkyl, or acyl;

--- =single or non-cumulated double bond, with the provisos that a double bond of the cis configuration is present between carbons 4 and 5; and that if a double bond is present between carbons 13 and 14, it is of the trans configuration;

X=(CH₂)_q or (CH₂)_qO; where q=1–6; and

Y=a phenyl ring optionally substituted with alkyl, halo, trihalomethyl, alkoxy, acyl, acyloxy, amino, alkylamino, acylamino, or hydroxy; or X—Y=(CH$_2$)$_p$Y$^1$; where p=0–6; and

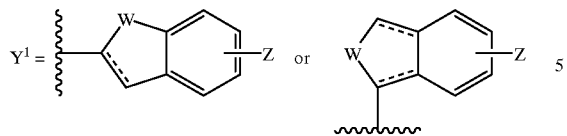

wherein:
W=CH$_2$, O, S(O)$_m$, NR$^9$, CH$_2$CH$_2$, CH=CH, CH$_2$O, CH$_2$S(O)$_m$, CH=N, or CH$_2$NR$^9$; where m=0–2, and R$^9$=H, alkyl, or acyl;
Z=H, alkyl, alkoxy, acyl, acyloxy, halo, trihalomethyl, amino, alkylamino, acylamino, or hydroxy; and
- - - =single or double bond.

19. A compound of formula II:

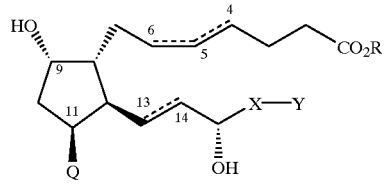

wherein:
R=H or alkyl;
- - - =single or non-cumulated double bond, with the provisos that a double bond of the cis configuration is present between carbons 4 and 5; and that if a double bond is present between carbons 13 and 14, it is of the trans configuration;
Q=Cl or F;
X=CH$_2$CH$_2$ or CH$_2$O; and
Y=phenyl, optionally substituted with halo or trihalomethyl; or
X—Y=(CH$_2$)$_p$Y$^1$; where p=0; and;

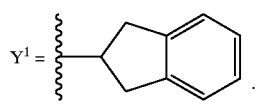

20. The compound of claim 19, wherein:
R=C$_2$–C$_4$ alkyl;
X=CH$_2$O; and
Y=substituted phenyl, where the substituent is selected from the group consisting of chloro and trifluoromethyl.

21. The compound of claim 20, having the formula:

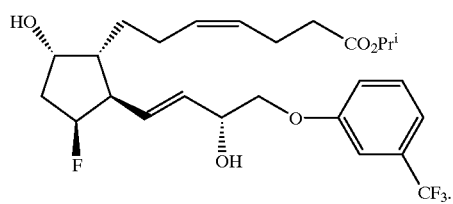

22. The compound of claim 20, having the formula:

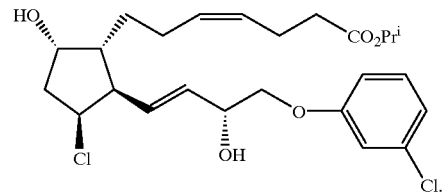

23. An ophthalmic composition for the treatment of glaucoma and ocular hypertension, comprising a compound of formula I:

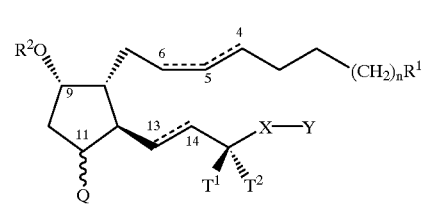

wherein:
n=0 or 2;
R$^1$=CO$_2$R, CONR$^4$R$^5$, CH$_2$OR$^6$, or CH$_2$NR$^7$R$^8$; where:
R=H or cationic salt moiety, or CO$_2$R forms an ophthalmically acceptable ester moiety;
R$^4$, R$^5$=same or different=H or alkyl; R$^6$=H, acyl, or alkyl;
R$^7$, R$^8$=same or different=H, acyl, or alkyl; with the proviso that if one of R$^7$, R$^8$=acyl, then the other=H or alkyl;
Q=halo;
one of T$^1$, T$^2$=H, and the other=OR$^3$, where R$^3$ is as defined below; or T$^1$ and T$^2$ together=O;
R$^2$, R$^3$=same or different=H, alkyl, or acyl;
- - - =single or non-cumulated double bond, with the proviso that a double bond of the cis configuration is present between carbons 4 and 5; and that if a double bond is present between carbons 13 and 14, it is of the trans configuration;
X=(CH$_2$)$_q$ or (CH$_2$)$_q$O; where q=1–6; and
Y=a phenyl ring optionally substituted with alkyl, halo, trihalomethyl, alkoxy, acyl, acyloxy, amino, alkylamino, acylamino, or hydroxy; or
X—Y=(CH$_2$)$_p$Y$^1$; where p=0–6; and

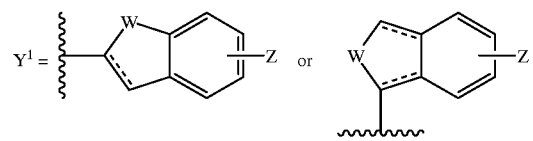

wherein:
W=CH$_2$, O, S(O)$_m$, NR$^9$, CH$_2$CH$_2$, CH=CH, CH$_2$O, CH$_2$S(O)$_m$, CH=N, or CH$_2$NR$^9$; where m=0–2, and R$^9$=H, alkyl, or acyl;
Z=H, alkyl, alkoxy, acyl, acyloxy, halo, trihalomethyl, amino, alkylamino, acylamino, or hydroxy; and
- - - =single or double bond;
and an ophthalmically acceptable vehicle therefor.

24. The composition of claim 23, wherein the compound is of the following formula:

39
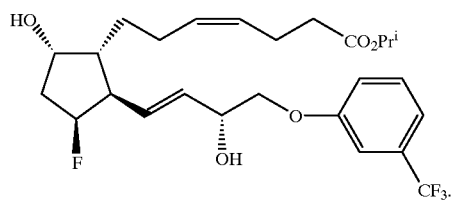
25. The composition of claim 23, wherein the compound is of the following formula:
40
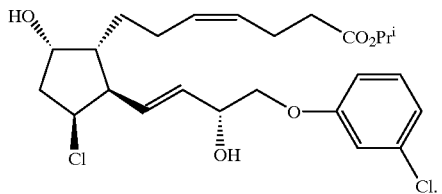
* * * * *